(12) United States Patent
Gluckman et al.

(10) Patent No.: US 7,714,020 B2
(45) Date of Patent: *May 11, 2010

(54) TREATMENT OF NON-CONVULSIVE SEIZURES IN BRAIN INJURY USING G-2-METHYL-PROLYL GLUTAMATE

(75) Inventors: Peter David Gluckman, Auckland (NZ); Margaret Anne Brimble, Auckland (NZ); Douglas Wilson, Taupo (NZ); Frank Casper Tortella, Columbia, MD (US); Anthony Joseph Williams, Middletown, MD (US); Xi-Chun May Lu, Laurel, MD (US); Jed A. Hartings, Silver Spring, MD (US); Divina Gryder, Potomac Falls, VA (US)

(73) Assignee: Neuren Pharmaceuticals Limited, Auckland (NZ)

( * ) Notice: Subject to any disclaimer, the term of this patent is extended or adjusted under 35 U.S.C. 154(b) by 873 days.

This patent is subject to a terminal disclaimer.

(21) Appl. No.: 11/398,032

(22) Filed: Apr. 4, 2006

(65) Prior Publication Data
US 2006/0251649 A1    Nov. 9, 2006

Related U.S. Application Data

(63) Continuation-in-part of application No. 10/155,864, filed on May 24, 2002, now Pat. No. 7,041,314, and a continuation-in-part of application No. 11/314,424, filed on Dec. 20, 2005, now Pat. No. 7,605,177, which is a continuation-in-part of application No. 10/155,864, application No. 11/398,032, which is a continuation-in-part of application No. 11/315,784, filed on Dec. 21, 2005, which is a continuation-in-part of application No. 10/155,864.

(60) Provisional application No. 60/293,853, filed on May 24, 2001.

(51) Int. Cl.
    *A61K 31/401*    (2006.01)
    *C07D 207/16*    (2006.01)

(52) U.S. Cl. ............... 514/423; 548/537; 424/451; 424/464

(58) Field of Classification Search ........... 548/537; 514/423; 424/451, 464
    See application file for complete search history.

(56) References Cited

U.S. PATENT DOCUMENTS

| 4,444,879 A | 4/1984 | Foster et al. |
| 4,511,390 A | 4/1985 | Kauer et al. |
| 4,699,875 A | 10/1987 | Appel et al. |
| 4,783,524 A | 11/1988 | Larsen et al. |
| 4,906,614 A | 3/1990 | Giertz et al. |
| 5,068,224 A | 11/1991 | Fryklund et al. |
| 5,089,406 A | 2/1992 | Williams et al. |
| 5,093,317 A | 3/1992 | Lewis et al. ............ 514/12 |
| 5,106,832 A | 4/1992 | Froesch et al. |
| 5,114,840 A | 5/1992 | Tryggvason et al. |
| 5,149,657 A | 9/1992 | Maugh et al. |
| 5,243,038 A | 9/1993 | Ferrari et al. |
| 5,273,961 A | 12/1993 | Clark et al. |
| 5,420,112 A | 5/1995 | Lewis et al. |
| 5,451,660 A | 9/1995 | Builder et al. |
| 5,496,712 A | 3/1996 | Cappello et al. |
| 5,635,604 A | 6/1997 | Dalboge et al. |
| 5,639,729 A | 6/1997 | Goldstein et al. |
| 5,648,335 A | 7/1997 | Lewis et al. |
| 5,670,616 A | 9/1997 | Weber |
| 5,679,552 A | 10/1997 | Dalboge et al. |
| 5,686,423 A | 11/1997 | Wang et al. |
| 5,691,169 A | 11/1997 | Dalboge et al. |
| 5,703,045 A | 12/1997 | Lewis et al. |
| 5,710,252 A | 1/1998 | Weber et al. |
| 5,714,460 A | 2/1998 | Gluckman et al. |
| 5,750,376 A | 5/1998 | Weiss et al. |
| 5,801,045 A | 9/1998 | Weber et al. |
| 5,804,550 A | 9/1998 | Bourguignon et al. |
| 5,804,563 A | 9/1998 | Still et al. |
| 5,861,373 A | 1/1999 | Gluckman et al. |
| 5,965,531 A | 10/1999 | Webster et al. ............ 514/12 |
| 6,054,579 A | 4/2000 | Harriman ............ 540/200 |
| 6,187,906 B1 | 2/2001 | Guan et al. ............ 530/331 |
| 6,294,585 B1 | 9/2001 | Brown |
| 6,342,585 B1 | 1/2002 | Grossmann |
| 6,365,573 B1 | 4/2002 | Gluckman et al. ......... 514/18 |
| 6,444,657 B1 | 9/2002 | Slusher et al. |
| 6,682,753 B2 | 1/2004 | Alexi ............ 424/422 |
| 2001/0018199 A1 | 8/2001 | Dalboge et al. |
| 2002/0013277 A1 | 1/2002 | Gluckman et al. |
| 2002/0035066 A1 | 3/2002 | Gluckman et al. |
| 2002/0115594 A1 | 8/2002 | Bourguignon |
| 2002/0151522 A1 | 10/2002 | Alexi |
| 2002/0177239 A1 | 11/2002 | Thomas et al. |
| 2003/0027755 A1 | 2/2003 | Guan et al. |
| 2003/0105072 A1 | 6/2003 | Degenhardt et al. |
| 2003/0211990 A1 | 11/2003 | Sieg et al. |

FOREIGN PATENT DOCUMENTS

EP    227619    1/1987

(Continued)

OTHER PUBLICATIONS

Anthony J. Williams, et al., "Characterization of a New Rat Model of Penetrating Ballistic Brain Injury", Jnl. of Neurotrauma, MD, vol. 22, No. 2, 2005, pp. 314-332.

Jed A. Hartings, et al, "Occurrence of nonconclusive seizures, periodic epileptiform discharges, and intermittent rhythmic delta activity in rat focal ischemia", Experimental Neurology 179 (2003) pp. 139-149.

(Continued)

*Primary Examiner*—Rebecca L Anderson
(74) *Attorney, Agent, or Firm*—D. Benjamin Borson

(57) ABSTRACT

Aspects of this invention include the use of G-2MePE to treat patients with brain injury characterized by non-convulsive seizures. G-2MePE is useful in treating brain injuries caused by traumatic brain injury, stroke, hypoxia/ischemia and toxic injury.

19 Claims, 32 Drawing Sheets

FOREIGN PATENT DOCUMENTS

| EP | 289314 | 2/1988 |
|---|---|---|
| EP | 308386 | 3/1989 |
| EP | 366638 | 5/1990 |
| EP | 357240 | 1/1993 |
| EP | 1043027 | 11/2000 |
| FR | 2707170 | 1/1995 |
| WO | WO 88/03533 | 5/1988 |
| WO | WO 88/08848 | 11/1988 |
| WO | WO 88/09171 | 12/1988 |
| WO | WO 89/01343 | 2/1989 |
| WO | WO 89/05822 | 6/1989 |
| WO | WO 90/05177 | 5/1990 |
| WO | WO 92/09695 | 6/1992 |
| WO | WO 93/02695 | 2/1993 |
| WO | WO 93/08826 | 5/1993 |
| WO | WO 93/08828 | 5/1993 |
| WO | WO 93/10806 | 6/1993 |
| WO | WO 93/20836 | 10/1993 |
| WO | WO 93/21216 | 10/1993 |
| WO | WO 94/23754 | 10/1994 |
| WO | WO 94/26301 | 11/1994 |
| WO | PCT/NZ 94/00143 | 12/1994 |
| WO | WO 95/13823 | 5/1995 |
| WO | WO 95/17204 | 6/1995 |
| WO | WO 97/17090 | 5/1997 |
| WO | WO 97/39032 | 10/1997 |
| WO | WO 97/47735 | 12/1997 |
| WO | WO 98/14202 | 4/1998 |
| WO | WO 98/52620 | 11/1998 |
| WO | WO 99/08702 | 2/1999 |
| WO | WO 99/15192 | 4/1999 |
| WO | WO 99/39210 | 8/1999 |
| WO | WO 99/65509 | 12/1999 |
| WO | WO 00/13650 | 3/2000 |
| WO | WO 02/16408 | 2/2002 |
| WO | WO 02/094856 | 11/2002 |

OTHER PUBLICATIONS

P.M. Vespa, MD, et al., "Acute seizures after intracerebral hemorrhage—A factor in progressive midline shift and outcome", Division of Neurosurgery, Department of Neurology, UCLA Stroke Center, Jan. 20, 2003, pp. 1441-1446.

Michael Privitera, et al., "EEG detection of nontonic-clonic status epilepticus in patients with altered consciousness", Department of Neurology, University of Cincinnati Medical Center, Feb. 16, 1994, pp. 155-166.

Paul M. Vespa, M.D., et al., "Increased incidence and impact of nonconvulsive and convulsive seizures after traumatic brain injury as detected by continuous electroencephalographic monitoring", J. Neurosurg vol. 91:750-760, 1999.

Lu, X.-C, A Glypromate Analog, NNZ-2566, is Neuroprotective in Rats Subjected to Penetrating Ballistic-Like Brain Injury (PBBI), Div. Psychiatry and Neuroscience, Walter Reed Army Institute of Research, Silver Spring, MD, 20910, Journal of Neurotrauma, vol. 10 (#22), p. 1255, Oct. 2005.

Notification of Transmittal of The International Search Report and The Written Opinion of the International Searching Authority; International Bureau dated Apr. 24, 2007 in International Application No. PCT/US06/19909.

Lucas, M.D., D. R., et. al., "The Toxic Effect of Sodium $_L$-Glutamate on the Inner Layers of the Retina", Archives of Opthamology, 58, 1957, pp. 198-204.

Curtis, David R., et. al., "Amino Acid Transmitters in the Mammalian Central Nervous System", Ergebnisse der Physiologie, 69, 1974, pp. 97-188.

Bauer, Carl-Axel, "Active Centers of α-Chymotrypsin and of Streptomyces griseus Proteases 1 and 3," Department of Biochemistry, University of Lund, Nov. 5, 1979, pp. 565-570.

Carone, R.A. et al., "Differences Between in vitro and in vivo Degradation of LHRH by Rat Brain and Other Organs," American Journal of Physiology, 253, 1987, E317-E321.

Szabo, Laszlo, et. al., "The Bovine Insulin-like Growth Factor (IGF) Binding Protein Purified from Conditioned Medium Requires the N-Terminal Tripeptide in IGF-1 for Binding," Biochemical and Biophysical Research Communications, vol. 151, No. 1, Feb. 29, 1988, pp. 207-214.

Shepard, M.D., Gordon M.,"Neurotransmitters and Neuromodulators," Neurobiology, $2^{nd}$ edition, 1988, pp. 145-176.

Sakaki, Atsushi, et al., "Multiple Forms of Immunoreative Growth Hormone-Releasing Hormone in Human Plasma, Hypothalamus, and Tumor Tissues," Journal of Clinical Endocrinolgy and Metabolism, vol. 68, No. 1, 1989, pp. 180-185.

Bourguignon, Jean-Pierre, et. al., "Pulsatile Release of Gonadortropin-Releasing Hormone from Hypothalamic Explants is Restrained by Blockade of $N$-Methyl-$_{D,L}$-Aspartate Receptors," Endocrinology, vol. 125, No. 2, 1989, pp. 1090-1096.

Sara, Vicki R., et. al., "Identification of Gly-Pro-Glu (GPE), the Aminoterminal Tripeptide of Insulin-like Growth Factor 1 Which is Truncated in Brain, as a Novel Neuroactive Peptide," Biochemical and Biophysical Research Communications, vol. 165, No. 2, Dec. 15, 1989, pp. 766-771.

Donoso, Alfredo O., et. al., "Glutamate Receptors of the Non-$N$-Methyl-$_D$-Aspartic Acid Type Mediate the Increase in Luteinizing Hormone-Releasing Hormone Release by Excitatory Amino Acids in Vitro", Endocrinology, vol. 126, No. 1, 1990, pp. 414-420.

Bourguignon, Jean-Pierre, et. al., "Maturation of the Hypothalamic Control of Pulsatile Gonadotropin-Releasing Hormone Secretion at Onset of Puberty: II. Reduced Potency of an Inhibitory Autofeedback," Endocrinology, vol. 127, No. 6, 1990, pp. 2884-2890.

Challis, Brian C., et al., "Synthesis and Characterisation of Some New $N$-Nitrosodipeptides," J. Chemistry Society Perkin Trans., 1990, pp. 3103-3108.

Sara, Vicki R., et al., "Neuroactive Products of IGF-1 and IGF-2 Gene Expression in the CNS," Molecular Biology and Physiology of Insulin and Insulin-Like Growth Factors, New York, 1991, pp. 439-448.

Hiney, Jill K., et al., "Insulin-Like Growth Factor I: A Possible Metabolic Signal Involved in the Regulation of Female Puberty," Neuroendocrinology, 54, 1991, pp. 420-423.

Bourguignon, Jean-Pierre, et. al., "Gonadal-Independent Developmental Changes in Activation of N-Methyl-D-Aspartate Receptors Involved in Gonadotropin-Releasing Hormone Secretion," Neuroendocrinology, 55, 1992, pp. 634-641.

Guan, Jian, et. al., "The Effects of IGF-1 Treatment After Hypoxic-Ischemic Brain Injury in Adult Rats," J Cereb Blood Flow Metab, vol. 13, No. 4, 1993, pp. 609-616.

Nilsson-Hakansson, Lena, et al., "The Effects of 1GF-1, Truncated IGF-1 and the Tripeptide Gly-Pro-Glu on Acetylcholine Release from Parietal Cortex of Rat Brain," NeuroReport, vol. 4, No. 9, Aug. 6, 1993, pp. 1111-1114.

Di Blasio,B., et al. "β-Alanine Containing Peptides: γ-Turns in Cyclotetrapeptides," Research Center on Bioactive Peptides, Napoli, Italy, Biopolymers, vol. 33, 1993, pp. 621-631.

Sara, Vicki R., et. al., "The Biological Role of Truncated Insulin-like Growth Factor-1 and the Tripeptide GPE in the Central Nervous System," Annals of the New York Academy of Sciences, 692, 1993, pp. 183-191.

Bourguignon, Jean-Pierre et. al., "Gonadotropin Releasing Hormone Inhibitory Autofeedback by Subproducts Antagonist at N-Methly-D-Aspartate Receptors: A Model of Autocrine Regulation of Peptide Scretion," The Endocrine Society, vol. 134, No. 3, 1994, pp. 1589-1592. The Endocrine Society, vol. 132, No. 3, 1994, pp. 1589-1592.

Saura, J. et al., "Neuroprotecnve Effects of Gly-Pro-Glu, the N-terminal Tripeptide of IGF-1, in the Hippocampus in vitro," NeuroReport, vol. 10, No. 1, Jan. 1999, pp. 161-164.

Hanusch-Kompa and Ivar Ugi, "Multi-Component Reactions 13: Synthesis of γ-Lactams as Part of a Multi-Ring System Via Ugi-4-Centre-3-Component Reaction," Technische Universität München, Tetrahedron Letters 39, 1998, pp. 2725-2728.

SYNTHETIC ANALOGUES OF GPE

I. MODIFY GLYCINE RESIDUE

G*PE

II. MODIFY GLUTAMIC ACID RESIDUE

GPE* i. α-carboxylic acid residue
ii. γ-carboxylic acid residue
iii. GPE diesters

III. MODIFY PEPTIDE LINKAGES

GP*E and GPE# i. modify Pro - α-methylproline
ii. modify Glu - N-Methylglutamic acid
    α-Methylglutamic acid

MODIFY GLUTAMIC ACID RESIDUE

*α-carboxylic acid - modify to an amide*

*synthesis of amide*

MODIFY GLUTAMIC ACID RESIDUE

γ-carboxylic acid - modify to an amide synthesis of amide

MODIFY GLUTAMIC ACID RESIDUE
*reduce γ-carboxylic acid - lactone prodrug*

% Improvement on Foot Fault at 72h

% Reduction of Activated Microglia Cells

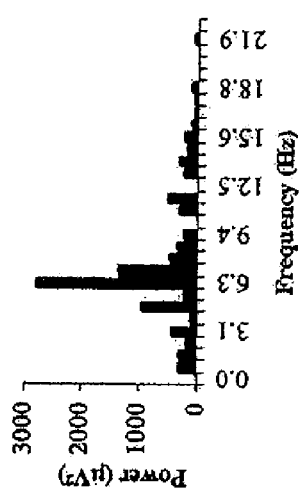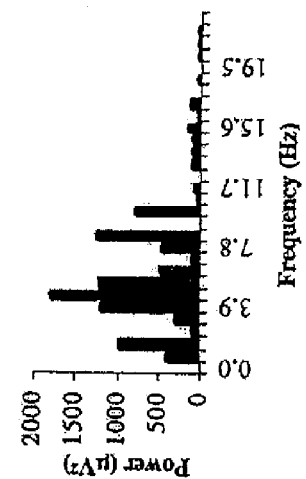
Fig. 22M
Fig. 22N
Prior Art

TREATMENT OF NON-CONVULSIVE SEIZURES IN BRAIN INJURY USING G-2-METHYL-PROLYL GLUTAMATE

CLAIM OF PRIORITY

This application is a Continuation-in-Part of U.S. patent application Ser. No. 10/155,864, filed May 24, 2002, now U.S. Pat. No. 7,041,314, issued May 9, 2006, which claims priority under 35 U.S.C. 119(e) to U.S. Provisional Patent Application No. 60/293,853, filed May 24, 2001.

This application is also a Continuation-in-Part of U.S. patent application Ser. No. 11/314,424, filed Dec. 20, 2005, entitled "Effects of Glycyl-2-Methyl Prolyl Glutamate on Neurodegeneration," Inventors: Gluckman et al., now U.S. Pat. No. 7,605,177 issued Oct. 20, 2009, which is a Continuation-in-Part of U.S. patent application Ser. No. 10/155,864, filed May 24, 2002, now U.S. Pat. No. 7,041,314, issued May 9, 2006, which claims priority under 35 U.S.C. 119(e) to U.S. Provisional Patent Application No. 60/293,853, filed May 24, 2001.

This application is also a Continuation-in-Part of U.S. patent application Ser. No. 11/315,784, entitled "Cognitive Enhancement and Cognitive Therapy Using Glycyl-L-2-Methyl Prolyl Glutamic Acid," Inventors: Gluckman et al., filed Dec. 21, 2005, which is a Continuation-in-Pan of U.S. patent application Ser. No. 11/314,424, filed Dec. 20, 2005, entitled "Effects of Glycyl-2-Methyl Prolyl Glutamate on Neurodegeneration," Inventors: Gluckman et al.; now U.S. Pat. No. 7,605,177 issued Oct. 20, 2009, which is a Continuation-in-Part of U.S. patent application Ser. No. 10/155,864, filed May 24, 2002 entitled "Effects of Glycyl-2-Methyl Prolyl Glutamate on Neurodegeneration," Inventors: Gluekman et al., now U.S. Pat. No. 7,041,314, issued May 9, 2006, which claims priority under 35 U.S.C. 119(e) to U.S. Provisional Patent Application No. 60/293,853, filed May 24, 2001. Each of the aforementioned applications and patents is expressly incorporated by reference.

BACKGROUND

1. Field of the Invention

This invention relates to analogs of glycyl-L-prolyl-L-glutamic acid (GPE). In particular, this invention relates to neuroprotective GPE analogs, to methods of making them, to pharmaceutical compositions containing them, and to their use in treating neurological disorders resulting from brain injury and characterized by non-convulsive brain seizures.

2. Description of Related Art

Each year approximately 1.5 million people in the U.S.A. sustain a traumatic brain injury with an estimated 1.0 million hospitalised. Of these, 225,000 are moderate to very severe and 50,000 result in death. These injuries can be caused by concussions, penetrating injury, contusions and diffuse axonal injury resulting from tearing of brain tissue. Traumatic brain injury is a difficult and often frustrating condition to treat. Blunt head trauma can result in brain hemorrhage, swelling and increased intracranial pressure. Penetrating wounds caused by projectiles can be particularly difficult because of the rapid absorption by brain tissues of a large amount of kinetic energy and the high degree of damage that can result. As a direct result of such injuries, brain cells can be damaged or die. Additionally, secondary effects can further exacerbate the loss of functional neurons. For example, cellular damage can release cytokines and other chemoattractive molecules into the brain and can cause inflammation. Inflammation itself can cause additional damage to brain tissues and cells through the release of proteases and other inflammatory mediators, which may recruit yet additional cell types and exacerbate the problems further.

Many attempts are made to reduce the severity of brain injury. Surgery can be used to remove projectiles, bone fragments or other debris from the brain. Additionally, surgery can be successful in certain cases to relieve increased intracranial pressure, which can cause additional nerve damage, either through a direct effect on pressure, or an effect related to changes in blood flow to affected portions of the brain. For example, a focal traumatic injury that causes bleeding or increased vascular permeability can produce an area of increased hydrostatic pressure. If the pressure is sufficiently high, blood flow to nearby portions of uninjured neural tissue can be reduced, compromising oxygenation of the affected tissue. Further, decreased blood flow, if severe enough, can cause starvation of brain tissues due to decreased flow of nutrients to the affected areas. As a result of these changes, in most patients with traumatic brain injury, recovery is often slow and incomplete. With prolonged periods of injury, neurological functions can be severely compromised and neural deficits may persist for many years, or even for the remainder of the patient's lifetime.

In addition to traumatic brain injury, stroke or severe hypoxia/ischemia can also result in brain injury. In many cases, patients with stroke exhibit similar signs and symptoms as patients with traumatic brain injury, including penetrating ballistic brain injury (PBBI). Further, perinatal asphyxia and coronary artery bypass graft (CABG) surgery, brain seizures and neurotoxic agents can lead to brain injury.

In many types of brain injury, neural deficits and neurological signs may be easy to evaluate. In some cases, impairment of motor function or abnormalities in electroencephalographic (EEG) signals is observed. In many animals and humans with traumatic brain injury, stroke or severe hypoxia/ischemia, a type of delayed EEG abnormality or brain seizure may evolve that is associated with overt motor convulsions and is therefore clearly identifiable by observers of such patients and thereby treatable with established anti-epileptic drug (AED) therapy.

However, in most cases of brain injury acute/early monitoring of EEG brain function is impossible or impractical. Here seizures may occur that are not associated with overt motor abnormalities. Without continuous EEG monitoring these "non-convulsive seizures" ("NCS") or "silent brain seizures" ("SBS") are not observed as a clinical feature of the brain trauma and go untreated. Nonetheless, such non-convulsive seizures can reflect severe brain injury. In one study, a subgroup of patients with severe traumatic brain injury experienced electroencephalographic signs of seizures, but had no convulsions (Vespa et al., J. Neurosurg 91:750-760 (1999), expressly incorporated herein fully by reference.

Non-convlusive seizures are not only symptomatic, but also can contribute to poor patient outcome. Thus, it is desirable to identify useful treatments for NCS. Although gabapentin and ethosuximide have been reported to reduce experimental NCS, many conventional antiepileptic agents are ineffective (Williams et al., J. Pharmacol. Exp. Therap. 311: 220-227 (2004), expressly incorporated herein fully by reference). Furthermore, efforts to treat NCS in human TBI with standard AED therapies have proven ineffective thereby identifying a critical care need in the art for improved methods of treating NCS.

It had been previously believed that mature nervous tissue is incapable of regeneration or recovery after severe injuries. Thus, few attempts have been made to treat brain damage to restore neural function. Fortunately, this misapprehension is being reversed, due in large part to recent studies on neural regeneration. For example, insulin-like growth factor 1 (IGF-1) has been shown to promote neural survival in animals with brain injuries. The N-terminal tripeptide of IGF-1, glycyl-prolyl-glutamate (Gly-Pro-Glu; GPE or Glypromate™) has similar neuroprotective effects. In fact, GPE has been used both in vitro and in vivo to treat neurodegeneration. However GPE is rapidly hydrolyzed by enzymes in plasma and in tissues thereby contributing to a relatively short half-life in vivo. Therefore, there is a great need for new types of therapies that can be used to treat neural damage associated with brain injuries resulting from stroke, various traumatic brain insults, coronary artery by-pass graft, hypoxic-ischemic episodes, etc.

EP 0 366 638 discloses GPE (a tri-peptide consisting of the amino acids Gly-Pro-Glu) and its di-peptide derivatives Gly-Pro and Pro-Glu. EP 0 366 638 discloses that GPE is effective as a neuromodulator and is able to affect the electrical properties of neurons.

WO95/172904 discloses that GPE has neuroprotective properties and that administration of GPE can reduce damage to the central nervous system (CNS) by the prevention or inhibition of neuronal and glial cell death.

WO 98/14202 discloses that administration of GPE can increase the effective amount of choline acetyltransferase (ChAT), glutamic acid decarboxylase (GAD), and nitric oxide synthase (NOS) in the central nervous system (CNS).

WO99/65509 discloses that increasing the effective amount of GPE in the CNS, such as by administration of GPE, can increase the effective amount of tyrosine hydroxylase (TH) in the CNS in order to increase TH-mediated dopamine production in the treatment of diseases such as Parkinson's disease.

WO02/16408 discloses GPE analogs capable of inducing a physiological effect equivalent to GPE within a patient. The applications of the GPE analogs include the treatment of acute brain injury and neurodegenerative diseases, including but not limited to, injury or disease in the CNS.

The disclosures of these and other documents referred to in this application (including in the Figures) are expressly incorporated herein by reference as if each one was individually incorporated by reference.

SUMMARY

To address the above and other problems in the art, we have recently discovered that an analog of GPE, namely glycyl-2-methylprolyl-glutamate (G-2MePE) has neuroprotective properties. We have unexpectedly found that G-2MePE can be used to protect neural tissue in animals with traumatic brain injuries, including penetrating brain injuries, stroke, hypoxia/ischemia and toxic injury. Furthermore, G-2MePE can be effective in reducing the incidence and severity of non-convulsive brain seizures, and can be effective in restoring motor coordination in animals with traumatic brain injury.

BRIEF DESCRIPTION OF THE DRAWINGS

This invention is described with reference to specific embodiments thereof. Other aspects and features of this invention can be understood with reference to the Figures, in which:

FIGS. 22A-22N depict typical EEG traces of NCS in the prior art. FIG. 22A shows a non-convulsive seizure (NCS) discharge in a rat with MCAo.

FIG. 22A shows a slow speed EEG tracing of a NCS, of contralateral (C) and injured hemispheres (I). Vertical lines represent 3-second intervals.

FIG. 22C (bottom traces) depict waveforms recorded from contralateral (C) and injured hemispheres (I). Vertical lines represent 3-second intervals. At termination, the seizure pattern generally became arrhythmic (FIG. 22D) with increased polyspike occurrence and decreasing discharge amplitude. No overt motor convulsions were visually observed during the electrographic seizures.

FIGS. 22M and 22N show power spectra of selected segments (e) and (f), respectively, of the EEG record marked in FIG. 22L above.

DETAILED DESCRIPTION

Definitions

Figure 1:
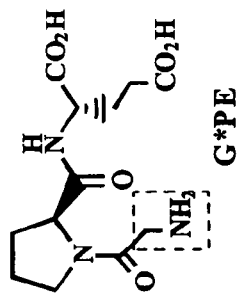
FIG. 1 is a general scheme for preparation of synthetic analogues of GPE of the invention.
Figure 1:
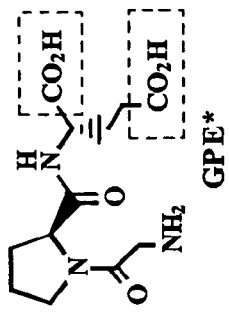
Figure 1:
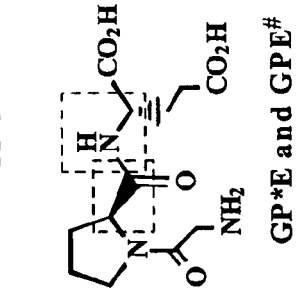
Figure 2:
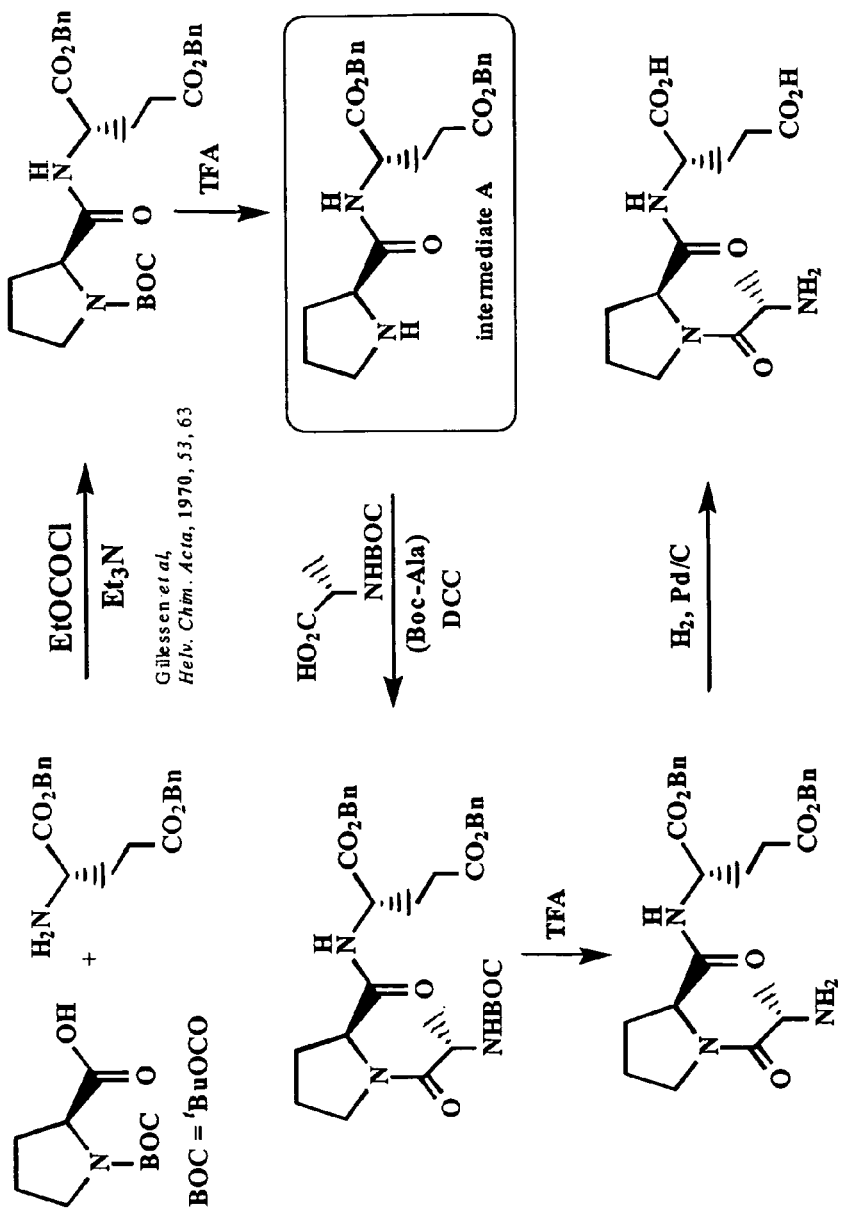
FIGS. 2 and 3 depict schemes for modifying glycine residues on GPE.
Figure 3:
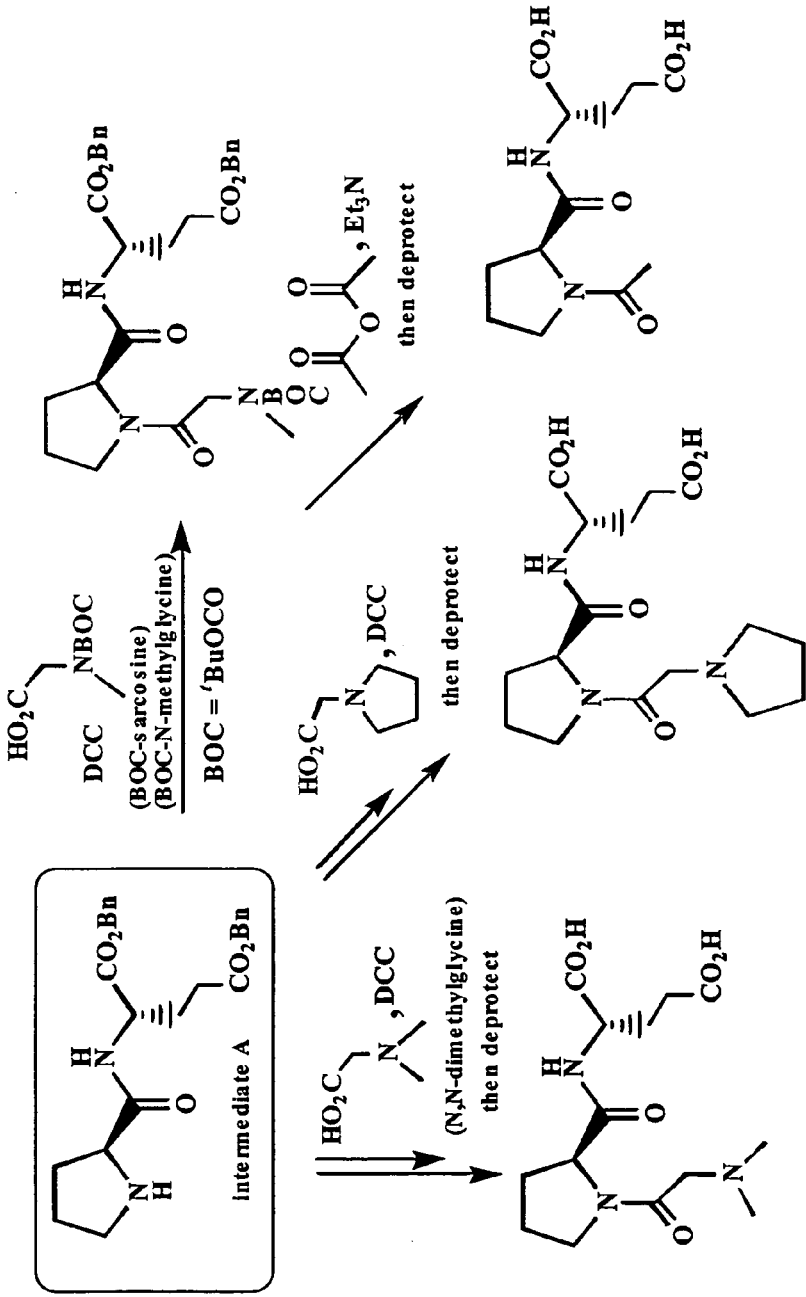
Figure 4:
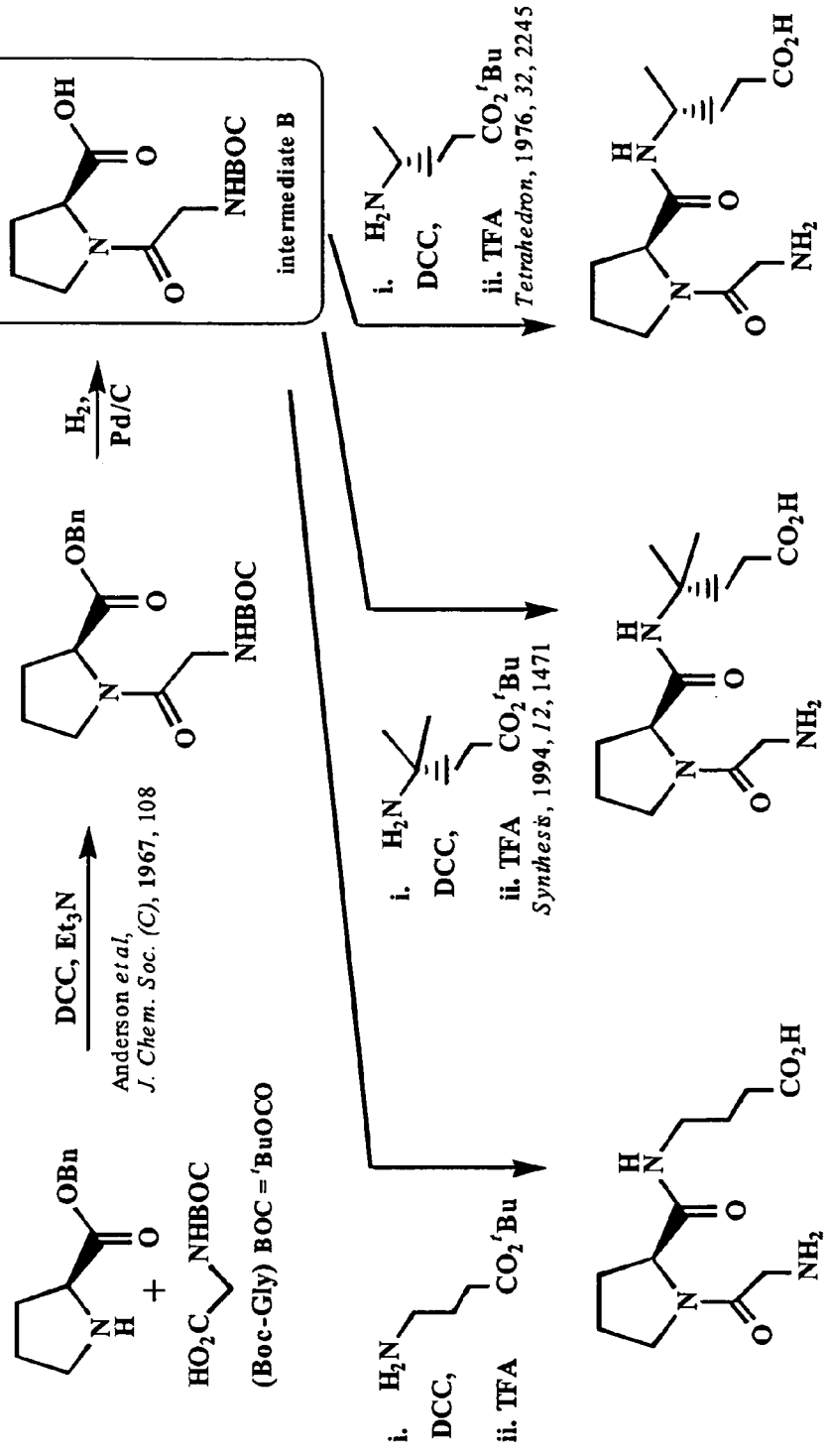
FIGS. 4 through 9 depict schemes for modifying glutamic acid residues of GPE.
Figure 5:
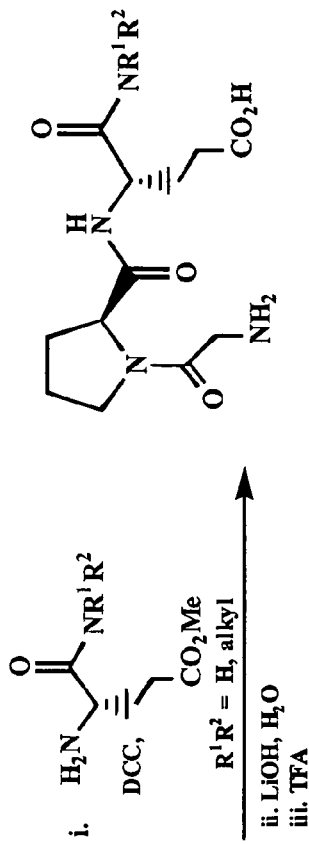
Figure 5:
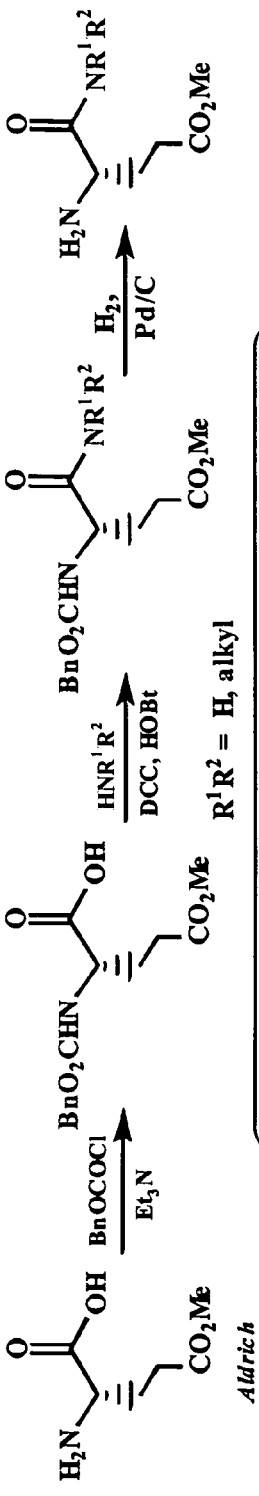
Figure 5:
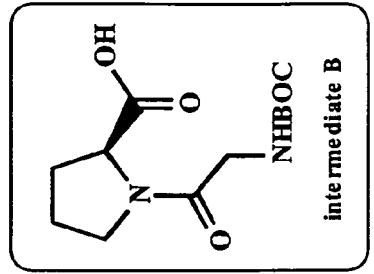
Figure 6:
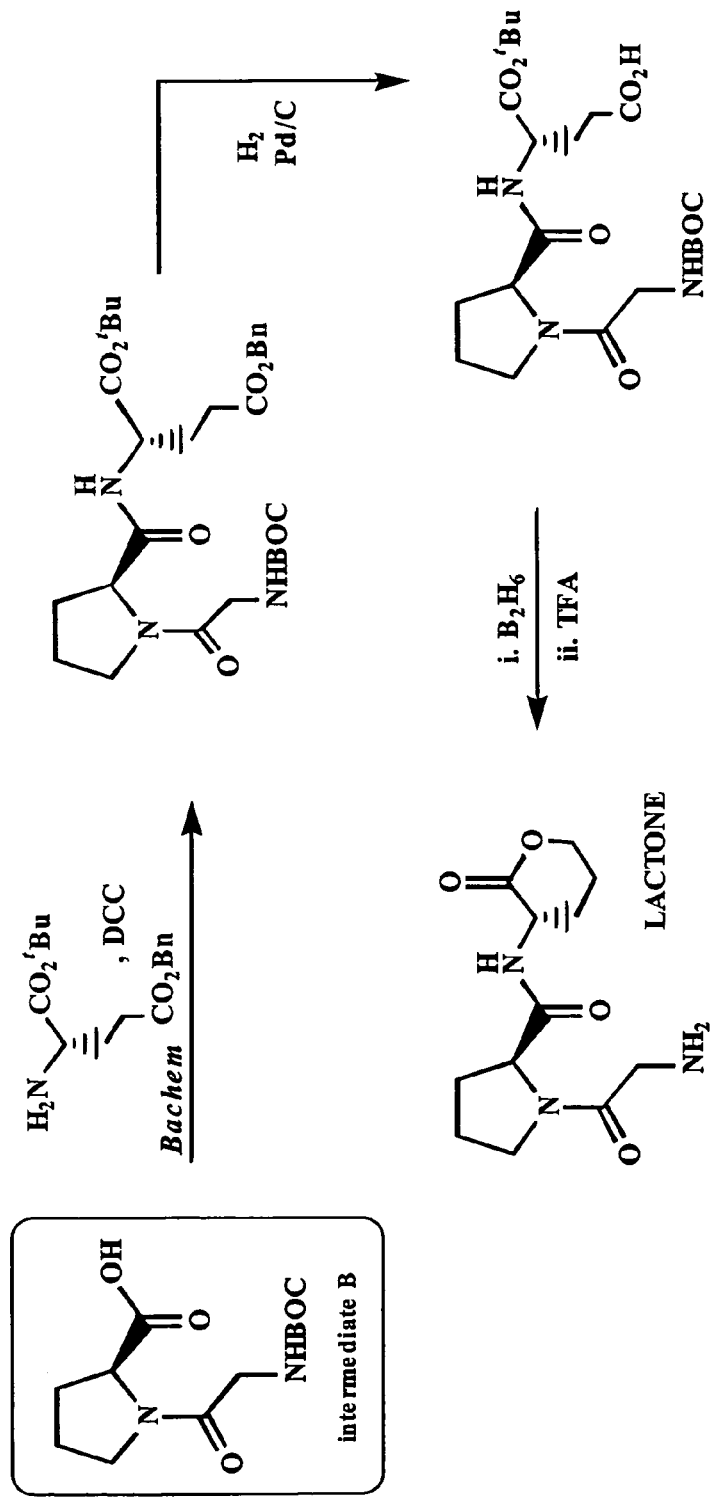
Figure 7:
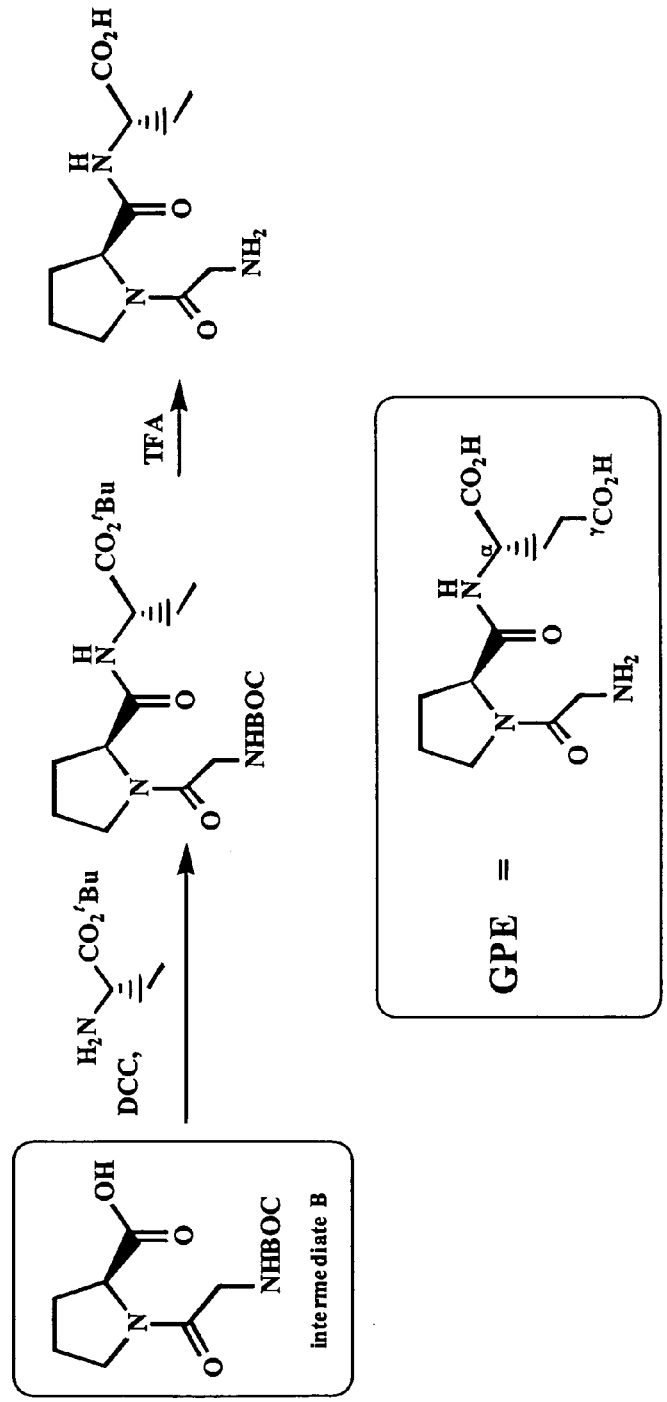
Figure 8:
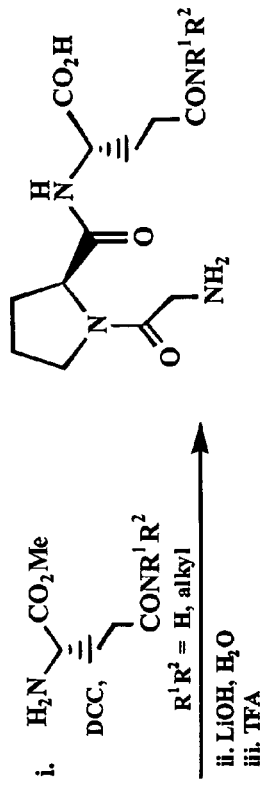
Figure 8:
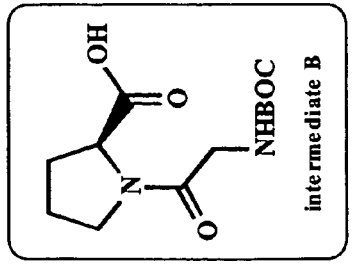
Figure 8:
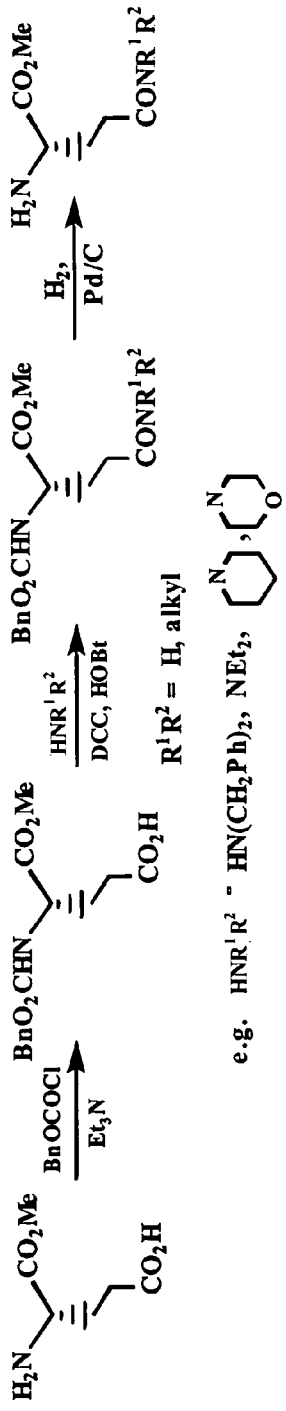
Figure 9:
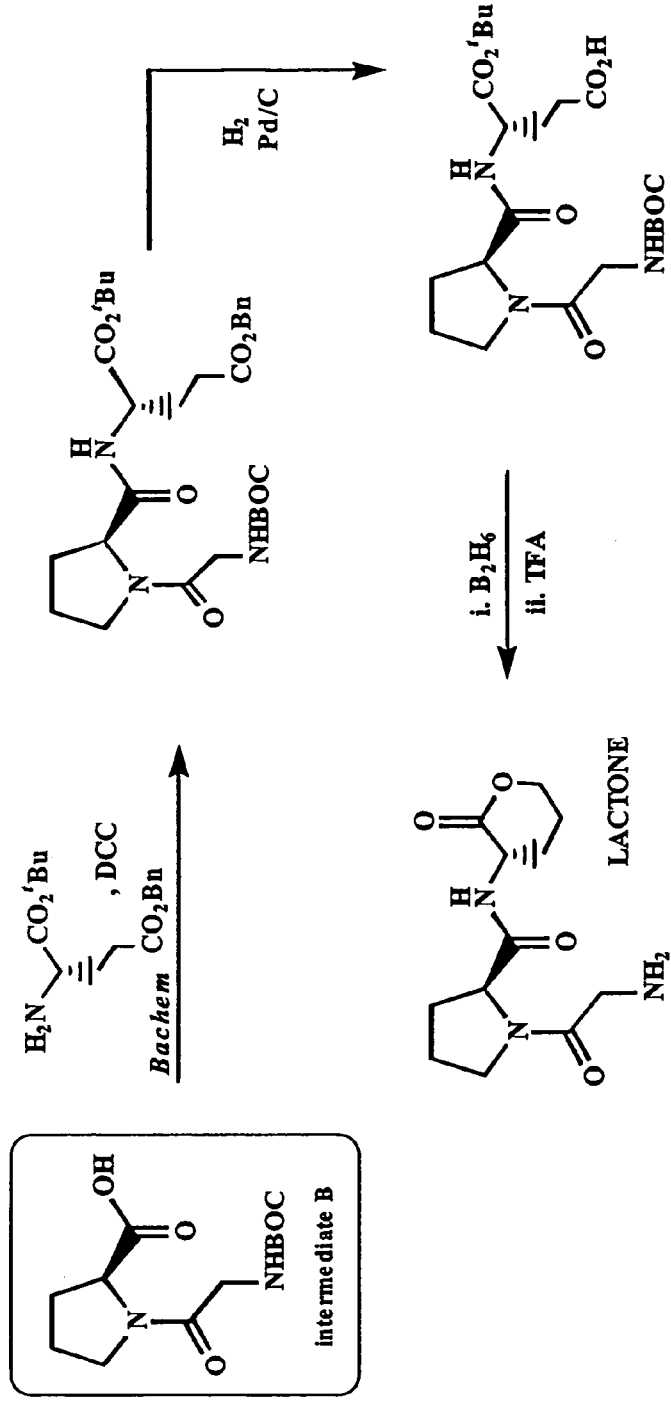
Figure 10:
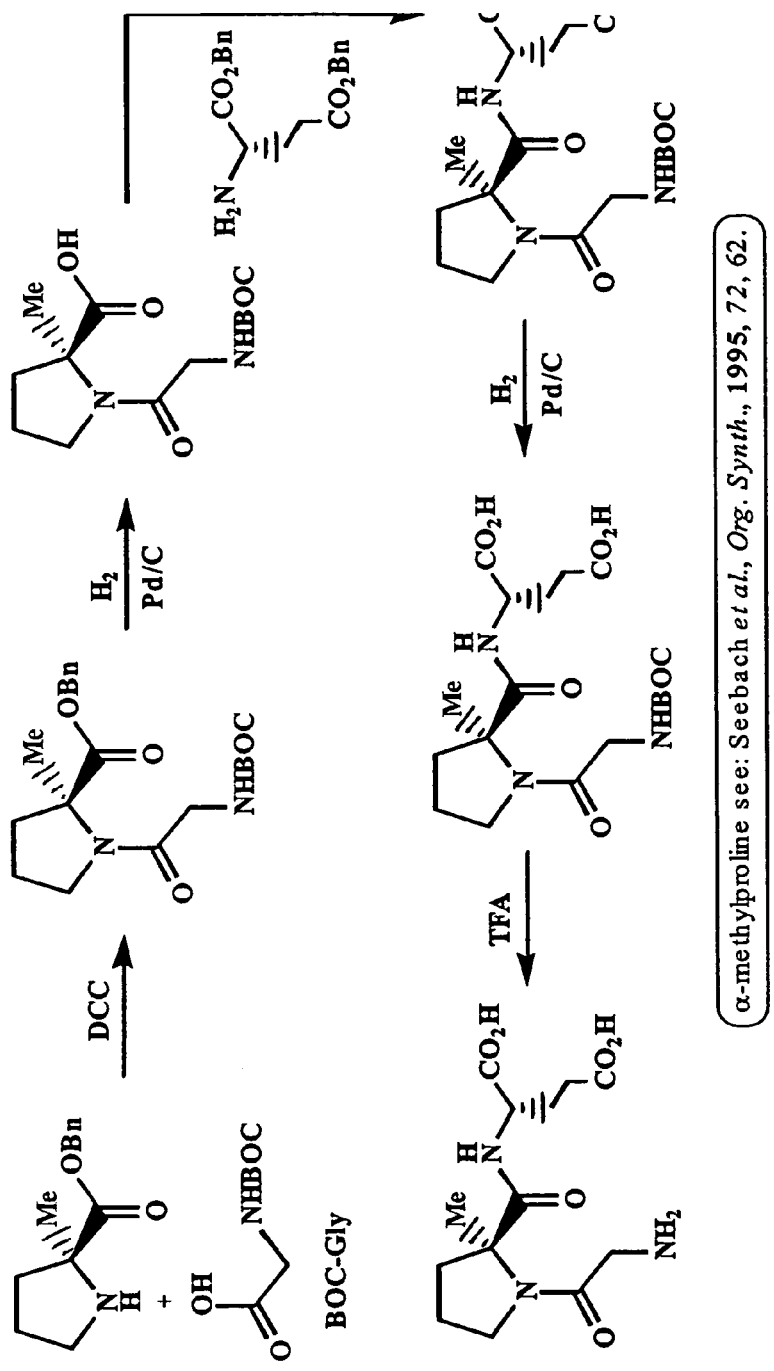
FIGS. 10 and 11 depict schemes for modifying peptide linkages of GPE.
Figure 11:
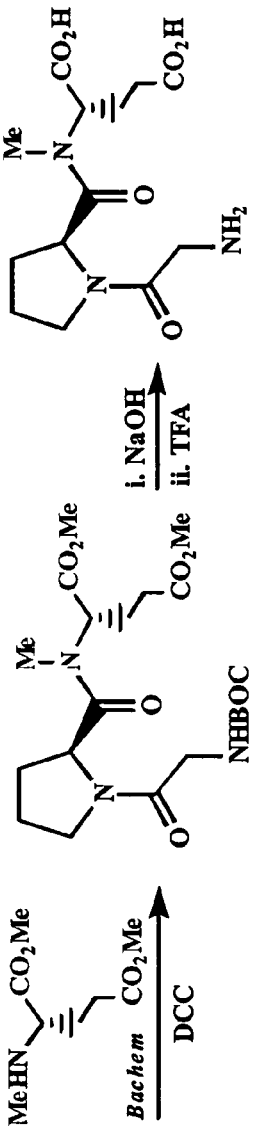

The term "about" with reference to a dosage or time refers to a particular variable and a range around that variable that is within normal measurement error or is within about 20% of the value of the variable.

The term "alkyl" means a linear saturated hydrocarbyl group having from one to six carbon atoms, or a branched or cyclic saturated hydrocarbyl group having from three to six carbon atoms. Exemplary alkyl groups include straight and branched chain, or cyclic alkyl groups, methyl, ethyl, isopropyl, cyclopropyl, tert-butyl, cyclopropylmethyl, and hexyl.

The term "animal" includes humans and non-human animals, such as domestic animals (cats, dogs, and the like) and farm animals (cattle, horses, sheep, goats, swine, and the like).

The term "aralkyl" means a group of the formula —$(CH_2)_{1-2}$Ar, where Ar is a 5- or 6-membered carbocyclic or heterocyclic aromatic ring, optionally substituted with 1 to 3 substituents selected from Cl, Br, —OH, —O-alkyl, —$CO_2R^8$ (where $R^8$ is H or alkyl), or —$NR^8R^9$, where $R^8$ is as described previously and $R^9$ is H or alkyl. Exemplary aralkyl groups include benzyl, 2-chlorobenzyl, 4-(dimethylamino)benzyl, phenethyl, 1-pyrrolylmethyl, 2-thienylmethyl, and 3-pyridylmethyl.

The term "disease" includes any unhealthy condition of an animal including particularly Parkinson's disease, Huntington's disease, Alzheimer's disease, multiple sclerosis, diabetes, motor disorders, seizures, and cognitive dysfunctions due to aging.

The term "fatty alcohol residue" is a linear hydrocarbyl group having from seven to twenty carbon atoms, optionally containing up to three carbon-carbon double bonds. Exemplary fatty alcohol residues include decyl, pentadecyl, hexadecyl (cetyl), octadecyl (stearyl), oleyl, linoleyl, and eicosyl.

The term "G-2MePE" or "Glycyl-2 Methyl Prolyl Glutamic Acid" means a modified tripeptide Glycyl-2-Methyl-L-Prolyl-L-Glutamic Acid. G-2MePE also includes the acid form Glycyl-2-Methyl Prolyl Glutamic Acid and the salt form, Glycyl-2-Methyl Prolyl Glutamate.

The term "growth factor" means an extracellular polypeptide-signaling molecule that stimulates a cell to grow or proliferate.

The term "injury" includes any acute damage of an animal including non-hemorrhagic stroke, traumatic brain injury, perinatal asphyxia associated with fetal distress such as that following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, cerebral trauma and toxic injury.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

The term "pharmaceutically acceptable salt" means a salt that is pharmaceutically acceptable and has the desired pharmacological properties. Such salts include salts that can be formed where acidic protons present in the compounds react with inorganic or organic bases. Suitable inorganic salts include those formed with the alkali metals, e.g. sodium and potassium, magnesium, calcium, and aluminium. Suitable organic salts include those formed with organic bases such as amines e.g. ethanolamine, diethanolamine, triethanolamine, tromethamine, N-methylglucamine, and the like. Salts also include acid addition salts formed by reaction of an amine group or groups present in the compound with an acid. Suitable acids include inorganic acids (e.g. hydrochloric and hydrobromic acids) and organic acids (e.g. acetic acid, citric acid, maleic acid, and alkane- and arene-sulfonic acids such as methanesulfonic acid and benzenesulfonic acid). When there are two acidic groups present in a compound, a pharmaceutically acceptable salt may be a mono-acid mono-salt or a di-salt; and similarly where there are more than two acidic groups present, some or all of such groups can be salified. The same reasoning can be applied when two or more amine groups are present in a compound.

The term "protecting group" is a group that selectively blocks one or more reactive sites in a multifunctional compound such that a chemical reaction can be carried out selectively on another unprotected reactive site and such that the group can readily be removed after the selective reaction is complete.

The term "therapeutically effective amount" means the amount of an agent that, when administered to an animal for treating a disease, is sufficient to effect treatment for that disease as measured using a test system recognized in the art.

The term "treating" or "treatment" of a disease may include preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "functional deficit" means a behavioral deficit associated with neurological damage. Such deficits include deficits of gait, as observed in patients with Parkinson's disease, motor abnormalities as observed in patients with Huntington's disease. Functional deficit also includes abnormal foot placement.

The term "seizure" means an abnormal pattern of neural activity in the brain that results in a motor deficit or lack of motor control resulting in abnormal motion, including spasmodic motion. "Seizure" includes electroencephalographic abnormalities, whether or not accompanied by abnormal motor activity.

The term "silent brain seizure" ("SBS") or "non-convulsive seizure" ("NCS") means an abnormal pattern of neural activity in the brain EEG that is defined by recurrent ictal spike, sharp, or slow wave discharges if different frequency patterns and complexes that is not accompanied by abnormal motor activity. Silent brain seizure may also include periodic lateralized epileptiform discharges ("PLEDs").

Implicit hydrogen atoms (such as hydrogen atoms on a pyrrolidine ring, etc.) are omitted from the formulae for clarity, but should be understood to be present.

Description of Embodiments

Non-convulsive seizures (NCS) can be present in patients having brain injuries caused by a variety of insults. In fact, some patients present with a history of brain injury but with few signs or symptoms. Thus, many of those patients are untreated or undertreated. Because NCS can lead to worsening in outcome, including more significant brain pathology and later neurological impairment, it can be important to intervene in treatment early after an insult that may lead to brain injury. Thus, a sub-group of patients with brain injury can be identified by the presence of non-convulsive brain seizures, even in the absence of motor or other frank neurological abnormalities. By diagnosing NCS at an early stage, patients can be treated and worsening of outcome be minimized, if not improved. Thus, in certain embodiments of this invention, patients with NCS can be treated effectively with G-2MePE, decreasing the overall severity of the SBS contribution to brain damage by 1) decreasing the incidence of NCS, and/or 2) increasing the time before NCS signs appear. This strategy can be useful in treating patients with stroke, hypoxia/ischemia, toxic and/or traumatic brain injury, including penetrating ballistic brain injury (PBBI).

Studies of stroke can be carried out using a well-characterized animal system in which a middle cerebral artery is occluded (MCAo). In animals with MCAo, a portion of the brain is deprived of oxygen, resulting in an infarct, similar to that seen in non-hemorrhagic stroke in human patients. Using this system, we have unexpectedly found that G-2MePE can decrease the incidence of NCS and can prolong the time period before which NCS signs appear. Similarly, hypoxia/ischemia can be studied in animal systems by temporarily or permanently occluding a carotid artery. We have previously demonstrated that G-2MePE can reduce the severity of neural degeneration in animals subjected to hypoxia/ischemia (U.S. application Ser. No. 10/155,864; U.S. application Ser. No. 11/314,424), both applications herein expressly incorporated fully by reference.

Penetrating ballistic brain injury (PBBI) has been more difficult to study due to the lack of suitable animal systems. However, with the recent development of an animal model system for generating and evaluating PBBI (Williams et al., Journal of Neurotrauma 22(2):314-332 (2005), expressly incorporated herein fully by reference, it is now possible to evaluate prospective therapies. Although PBBI has certain unique features, many of the signs and symptoms of PBBI are similar to those of other types of brain injuries including impairment if cerebral blood flow (cerebral ischemia) as may be encountered in clinical ischemic insults including stroke. For example, in an animal model of stroke (the system described in U.S. patent application Ser. No. 11/314,424), we found that motor deficits associated with loss of brain tissue caused by occlusion of the middle cerebral artery (MCAO) can be reduced by G-2MePE. Herein, we unexpectedly found that in other animals without motor seizure activity, G-2MePE can delay and in many cases prevent the appearance of NCS in animals with MCAo.

Animal Model System for Studying PBBI

With the development of an animal model for studying PBBI it is now possible to carry out careful studies of PBBI under controlled conditions. Briefly, the animal system was designed to mimic effects in human beings who suffer from PBBI, for example caused by a penetrating round (bullet). When a penetrating round enters the brain, the increased drag forces and yaw angle cause the round to tumble. During such unstable flight, an estimated 83% of the round's available energy is dissipated into the tissue, forming a large temporary cavity in the shape of an ellipsoid. This temporary cavity, which is estimated to be 10-20 times larger than the size of the permanent cavity caused by the missile track, compresses the surrounding tissue and is considered to be a major source of damage from a ballistic wound.

The penetrating ballistic brain injury model described in Williams et al (2005), which is that used in this application was designed to model two aspects of a high-energy bullet wound to the head: (1) the permanent injury tract created by the path of the bullet itself, and (2) the large temporary cavity generated by energy dissipation from the penetrating missile. The injury is produced by insertion of a specially designed probe into the brain of an anesthetized rat at the desired location (permanent injury tract) and rapid inflation of an attached balloon to mimic the temporary cavity induced by a penetrating bullet. Parameters for the size and shape of the temporary cavity were calculated based on the cavitation produced in the human brain by a NATO 7.62 mm round. The size of the probe and the volume of the expanded balloon were scaled to the rat brain by a ratio of 762.5:1. Due to the linear relationship between the bullet's impact velocity and the diameter of the temporary cavity, different injury severities can be modelled by expanding the balloon to different volumes.

As a result of such injuries, hemispheric swelling and intracranial pressure increases, reactive astrocytes increase in number, microglia and leukocyte infiltration is observed. Neurological tests and behavioural tests (e.g., balance beam test) demonstrate sensory-motor deficits. Additionally, severe, electroencephalographic disturbances occur, including the presence of cortical spreading depression, slow-waves and brain seizure activity. Thus, the rat system used herein is a reproducible system that produces quantifiable measures of outcome of PBBI and is scalable to the severity of injury. Thus, results obtained using this animal system closely mimic human PBBI, and studies using this system are therefore predictive of outcomes in humans. Additionally, this animal system can provide highly predictive results of studies on agents that protect neurons from damage caused by PBBI, making positive results obtained with G-2MePE highly predictive of effects that are expected in treating humans with G-2MePE.

Non-Convulsive Seizures

Brain injury can, in many cases, cause a type of seizure without motor effects. Such seizures, non-convulsive seizures (NCS), also known as silent brain seizures (SBS) have been observed in humans with severe traumatic brain injury (Vespa et al., J. Neurosurg 91:750-760 (1999). In these patients, many have abnormal electroencephalographic (EEG) activity that can be monitored using continuous EEG measurements. Such measurements show both epileptic types of activity, including a sudden onset of repetitive spike-and-wave discharges that can increase in amplitude and evolve over time. One type of EEG pattern is pseudoperiodic lateralized epileptiform discharges ("PLEDs"). Other subjects showed non-epileptiform discharges, including a symmetrical disorganized slowing in the 5 to 7 Hz range or asymmetrical disorganized delta waves. Importantly, although classical therapies for epileptiform EEG abnormalities (e.g., phenyloin, midazolam, lorazepam, phenobarbital and the like) may be effective in reducing delayed post-traumatic epileptiform abnormalities, those agents may not be effective by themselves in treating patients suffering from SBS.

Similarly, acute seizures can be observed after intracerebral hemorrhage (Vespa et al. Neurology 60:1441-1446 (2003). In a population of patients with ischemic stroke or intraparenchymal hemorrhage, EEG recordings showed electrographic seizures. Additionally, seizures after intercerebral hemorrhage may be of the non-convulsive type (NCS or SBS).

The types of EEG activity described for human are mimicked by similar epileptiform or NCS activity in rats (Hartings et al. Experimental Neurology 179:139-149 (2003). In rats subjected to middle cerebral artery occlusion (MCAo), EEG abnormalities include 1-3 Hz rhythmic spiking, PLEDs and intermittent rhythmic delta activity (IRDA). PLEDs were characterized by appearance of interictal spikes, sharp or slow waves recurring with a variable period of from 1 to 8 seconds. IRDA events were characterized by presence of readily identifiable, brief (e.g., <10 second) bursts of rhythmic, large-amplitude waves in the delta-theta (3 to 8 Hz) frequency range. In many cases, electrographic seizures were not associated with motor convulsant activity.

Thus, we can define a sub-population of patients with acute brain injury and the presence of NCS activity without overt motor manifestations. For example, a patient having a history of brain trauma or IRDA and PLEDs may be well suited for therapy with G-2MePE. In these patients, G-2MePE can be useful in decreasing the magnitude and number of NCS events, and thereby can decrease the likelihood of later neurological damage caused by NCS activity.

In some cases, it can be desirable to treat a subject experiencing NCS with G-2MePE and another agent to inhibit neurodegeneration. Several other neuroprotective agents are known in the art, and include Gly-Pro-Glu (GPE), insulin-like growth factor-I (IGF-I), insulin-like growth factor-II (IGF-II), transforming growth factor-.beta.1, activin, growth hormone, nerve growth factor, growth hormone binding protein, IGF-binding protein-3 (IGFBP-3], basic fibroblast growth factor, acidic fibroblast growth factor, hst/Kfgk gene product, FGF-3, FGF-4, FGF-6, keratinocyte growth factor, androgen-induced growth factor, int-2, fibroblast growth factor homologous factor-1 (FHF-1), FHF-2, FHF-3 and FHF-4, keratinocyte growth factor 2, glial-activating factor, FGF-10, FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), $\alpha$-, $\beta$, $\gamma$, or consensus interferon, TNF-$\alpha$, clomethiazole; kynurenic acid, Semax, tacrolimus, L-threo-1-phenyl-2-deca-noylamino-3-morpholino-1-propanol, adrenocorticotropin-(4-9) analog (ORG 2766), dizolcipine (MK-801), selegiline, glutamate antagonists NPS1506, GV1505260, MK-801, GV150526, AMPA antagonists 2,3-dihydroxy-6-nitro-7-sulfamoylbenzo(f)quinoxaline (NBQX), LY303070, LY300164, MAdCAM-1mAb, MECA-367 (ATCC accession no. HB-9478), an anti-α4β1 receptor antibody and an anti-α4β17 receptor antibody.

It can be appreciated that along with G-2MePE, classical anti-epileptic medications can be used if desired. Combination therapy using G-2MePE and one or more other anti-epileptic drugs (AEDs) can be of benefit in treating a non-convulsive event. Thus, in certain embodiments, one or more hydantoins, including phenyloin, fos-phenyloin, mephenyloin and ethotoin may be used along with G-2MePE. In other embodiments, one or more barbiturates, including phenobarbital, mephobarbital, primidone and its metabolite phenylethylmalonamide (PEMA) can be used along with G-2MePE. In still other embodiments, G-2MePE and one or more iminostilbenes, including carbamazepine, can be used, as well as one or more succinimides, including ethosuximide. Additionally, valproic acid and/or its salt valproate and G-2MePE can be used in combination to achieve desired therapeutic effects. In other situations, G-2MePE can be used with one or more oxazolidinediones, including trimethadione and paramethadione, one or more benzodiazepines, including clonazepam, clorazepate, lorazepam, diazepam and its metabolites N-desmethyldiazepam and oxazepam, gabapentin, lamotrigine, γ-vinyl gamma amino butyric acid (γ-vinyl GABA), one or more carbonic anhydrase inhibitors including acetazolamide, one or more dicarbamates including felbamate. In still further embodiments, G-2MePE can be used in combination with one or more agents including midazolam and dextromethorphan. It can be appreciated that G-2MePE can be used with one or more agents from different classes noted herein.

EXAMPLES

The following examples are intended to illustrate embodiments of this invention, and are not intended to limit the scope to these specific examples.

Example 1

Synthesis of
N,N-Dimethylglycyl-L-prolyl)-L-glutamic acid

The following non-limiting example illustrates the synthesis of a compound of the invention, N,N-Dimethylglycyl-L-prolyl-L-glutamic acid.

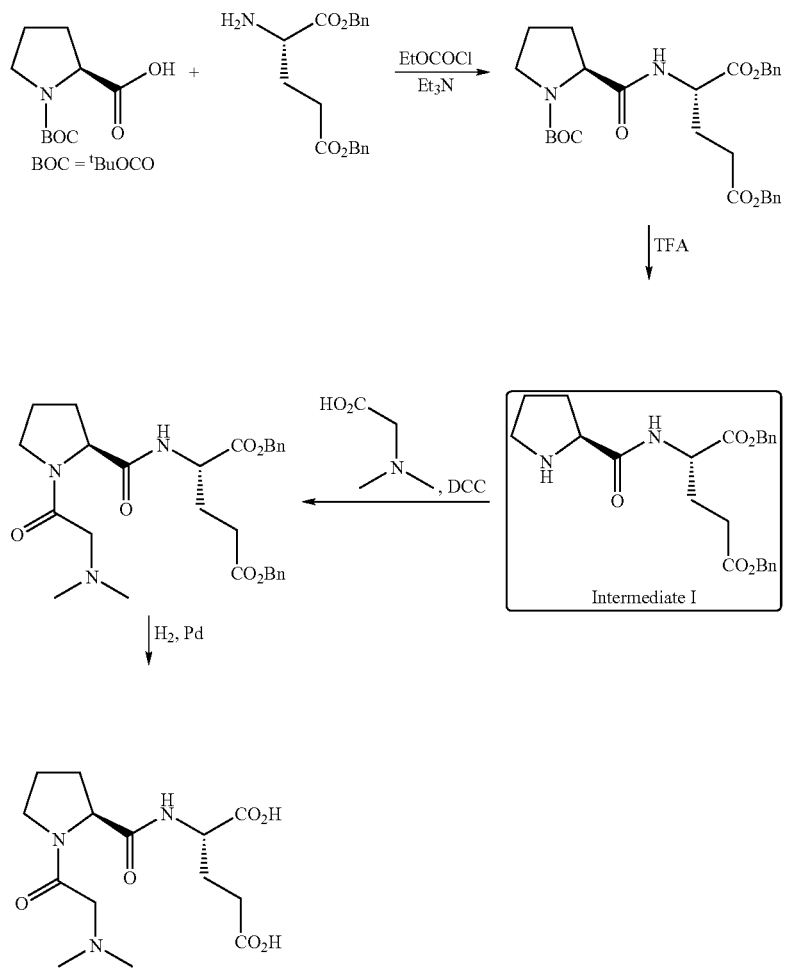

All starting materials and other reagents were purchased from Aldrich; BOC=tert-butoxycarbonyl; Bn=benzyl.

BOC-L-proline-(β-benzyl)-L-glutamic acid benzyl ester

To a solution of BOC-proline (Anderson G W and McGregor A C: J. Amer. Chem. Soc.: 79, 6810, 1994) (10 mmol) in dichloromethane (50 ml), cooled to 0° C., was added triethylamine (1.39 ml, 10 mmol) and ethyl chloroformate (0.96 ml, 10 mmol). The resultant mixture was stirred at 0° C. for 30 minutes. A solution of dibenzyl-L-glutamate (10 mmol) was then added and the mixture stirred at 0° C. for 2 hours then warmed to room temperature and stirred overnight. The reaction mixture was washed with aqueous sodium bicarbonate and citric acid (2 mol 1-1) then dried ($MgSO_4$) and concentrated at reduced pressure to give BOC-L-proline-L-glutamic acid dibenzyl ester (5.0 g, 95%).

L-proline-L-glutamic acid dibenzyl ester

A solution of BOC-L-glutamyl-L-proline dibenzyl ester (3.4 g, 10 mmol), cooled to 0° C., was treated with trifluoroacetic acid (25 ml) for 2 h. at room temperature. After removal of the volatiles at reduced pressure the residue was triturated with ether to give L-proline-L-glutamic acid dibenzyl ester.

N,N-Dimethylglycyl-L-prolyl-L-glutamic acid

A solution of dicyclohexylcarbodiimide (10.3 mmol) in dichloromethane (10 ml) was added to a stirred and cooled (0° C.) solution of L-proline-L-glutamic acid dibenzyl ester (10 mmol), N,N-dimethylglycine (10 mmol) and triethylamine (10.3 mmol) in dichloromethane (30 ml). The mixture was stirred at 0° C. overnight and then at room temperature for 3 h. After filtration, the filtrate was evaporated at reduced pressure. The resulting crude dibenzyl ester was dissolved in a mixture of ethyl acetate (30 ml) and methanol (30 ml) containing 10% palladium on charcoal (0.5 g) then hydrogenated at room temperature and pressure until the uptake of hydrogen ceased. The filtered solution was evaporated and the residue recrystallised from ethyl acetate to yield the tripeptide derivative.

It will be evident that following the method of the Example, and using alternative amino acids or their amides or esters, will yield other compounds of Formula 1.

Example 2

Synthesis of Glycyl-L-2-Methyl-L-Prolyl-L-Glutamate

Glycyl-L-2-Methylprolyl-L-Glutamic Acid (G-2MePE)

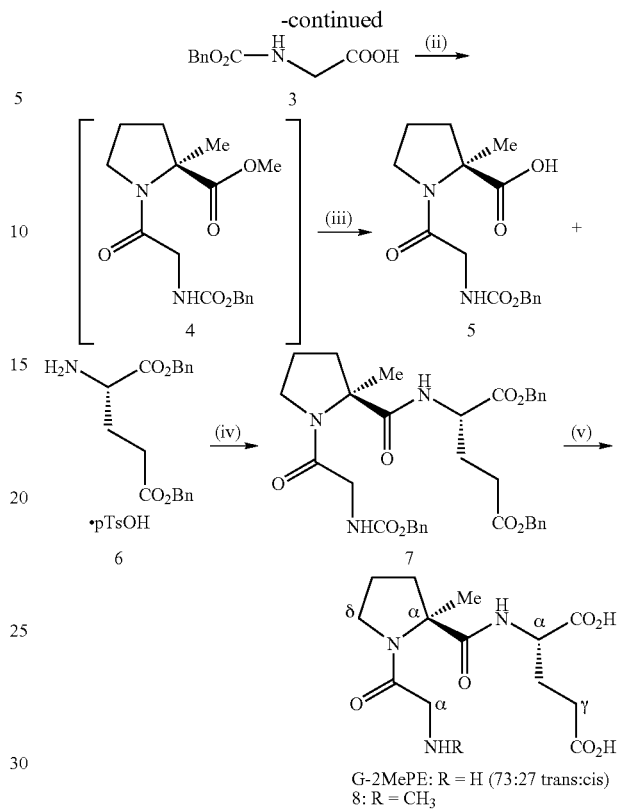

Reagents, conditions and yields:
(i) $SOCl_2$, MeOH, 79° C., $N_2$, 24 h (104%);
(ii) $Et_3N$, DCC, $CH_2Cl_2$, 0° C. to RT, $N_2$, 20 h;
(iii) 1M aq. NaOH, 1,4-dioxane, 19 h (60%, 2 steps);
(iv) $Et_3N$, BoPCl, $CH_2Cl_2$, RT, $N_2$, 17 h (89%);
(v) $H_2$, 10% Pd/C, 91:9 MeOH—$H_2O$, RT, 23 h (86%).

L-2-Methylproline and L-glutamic acid dibenzyl ester p-toluenesulphonate were purchased from Bachem, N-benzyloxycarbonyl-glycine from Acros Organics and bis(2-oxo-3-oxazolidinyl)phosphinic chloride (BpPCl, 97%) from Aldrich Chem. Co.

Methyl L-2-methylprolinate hydrochloride 2

Thionyl chloride (5.84 $cm^3$, 80.1 mmol) was cautiously added dropwise to a stirred solution of (L)-2-methylproline 1 (0.43 g, 3.33 mmol) in anhydrous methanol (30 $cm^3$) at −5° C. under an atmosphere of nitrogen. The reaction mixture was heated under reflux for 24 h, and the resultant pale yellow-coloured solution was concentrated to dryness in vacuo. The residue was dissolved in a 1:1 mixture of methanol and toluene (30 $cm^3$) then concentrated to dryness to remove residual thionyl chloride. This procedure was repeated twice more, yielding hydrochloride 2 (0.62 g, 104%) as an hygroscopic, spectroscopically pure, off-white solid: mp 127-131° C.; $[α]_D$ −59.8 (c 0.24 in $CH_2Cl_2$); $ν_{max}$ (film)/$cm^{-1}$ 3579, 3398 br, 2885, 2717, 2681, 2623, 2507, 1743, 1584, 1447, 1432, 1374, 1317, 1294, 1237, 1212, 1172, 1123, 981, 894, 861 and 764; $δ_H$ (300 MHz; $CDCl_3$; $Me_4Si$) 1.88 (3H, s, Proα-$CH_3$), 1.70-2.30 (3H, br m, Proβ-$H_AH_B$ and Proγ-$H_2$), 2.30-2.60 (1H, br m, Proβ-$H_AH_B$), 3.40-3.84 (2H, br m, Proδ-$H_2$), 3.87 (3H, s, $CO_2CH_3$), 9.43 (1H, br s, NH) and 10.49 (1H, br s, HCl); $δ_C$ (75 MHz; $CDCl_3$) 21.1 ($CH_3$, Proα-$CH_3$), 22.4 ($CH_2$, Proγ-C), 35.6 ($CH_2$, Proβ-C), 45.2 ($CH_2$, Proδ-C), 53.7 ($CH_3$, $CO_2CH_3$), 68.4 (quat., Proα-C) and 170.7 (quat., CO); m/z (FAB+) 323.1745 $[M_2·H^{35}Cl·H^+$: $(C_7H_{13}NO_2)_2$.

H$^{35}$Cl.H requires 323.1738] and 325.1718 [M$_2$.H$^{37}$Cl.H$^+$: (C$_7$H$_{13}$NO$_2$)$_2$. H$^{37}$Cl.H requires 325.1708].

N-Benzyloxycarbonyl-glycyl-L-2-methylproline 5

Anhydrous triethylamine (0.45 cm$^3$, 3.23 mmol) was added dropwise to a mixture of methyl L-2-methylprolinate hydrochloride 2 (0.42 g, 2.34 mmol) and N-benzyloxycarbonyl-glycine (98.5%) 3 (0.52 g, 2.45 mmol) in methylene chloride (16 cm$^3$), at 0° C., under an atmosphere of nitrogen. The resultant solution was stirred for 20 min and a solution of 1,3-dicyclohexylcarbodiimide (0.56 g, 2.71 mmol) in methylene chloride (8 cm$^3$) at 0° C. was added dropwise and the reaction mixture was warmed to room temperature and stirred for a further 20 h. The resultant white mixture was filtered through a Celite™ pad to partially remove 1,3-dicyclohexylurea, and the pad was washed with methylene chloride (50 cm$^3$). The filtrate was washed successively with 10% aqueous hydrochloric acid (50 cm$^3$) and saturated aqueous sodium hydrogen carbonate (50 cm$^3$), dried (MgSO$_4$), filtered, and concentrated to dryness in vacuo. Further purification of the residue by flash column chromatography (35 g SiO$_2$; 30-70% ethyl acetate-hexane; gradient elution) afforded tentatively methyl N-benzyloxycarbonyl-glycyl-L-2-methylprolinate 4 (0.56 g), containing 1,3-dicyclohexylurea, as a white semi-solid: R$_f$ 0.65 (EtOAc); m/z (EI+) 334.1534 (M$^+$. C$_{17}$H$_{22}$N$_2$O$_5$ requires 334.1529) and 224 (1,3-dicyclohexylurea).

To a solution of impure prolinate 4 (0.56 g, ca. 1.67 mmol) in 1,4-dioxane (33 cm$^3$) was added dropwise 1M aqueous sodium hydroxide (10 cm$^3$, 10 mmol) and the mixture was stirred for 19 h at room temperature. Methylene chloride (100 cm$^3$) was then added and the organic layer extracted with saturated aqueous sodium hydrogen carbonate (2×100 cm$^3$). The combined aqueous layers were carefully acidified with hydrochloric acid (32%), extracted with methylene chloride (2×100 cm$^3$), and the combined organic layers dried (MgSO$_4$), filtered, and concentrated to dryness in vacuo. Purification of the ensuing residue (0.47 g) by flash column chromatography (17 g SiO$_2$; 50% ethyl acetate-hexane to 30% methanol-dichloromethane; gradient elution) gave N-protected dipeptide 5 (0.45 g, 60%) as a white foam in two steps from hydrochloride 2. Dipeptide 5 was shown to be exclusively the trans-orientated conformer by NMR analysis: R$_f$ 0.50 (20% MeOH—CH$_2$Cl$_2$); [α]$_D$ −62.3 (c 0.20 in CH$_2$Cl$_2$); ν$_{max}$ (film)/cm$^{-1}$ 3583, 3324 br, 2980, 2942, 1722, 1649, 1529, 1454, 1432, 1373, 1337, 1251, 1219, 1179, 1053, 1027, 965, 912, 735 and 698; δ$_H$ (300 MHz; CDCl$_3$; Me$_4$Si) 1.59 (3H, s, Proα-CH$_3$), 1.89 (1H, 6 lines, J 18.8, 6.2 and 6.2, Proβ-H$_A$H$_B$), 2.01 (2H, dtt, J 18.7, 6.2 and 6.2, Proγ-H$_2$), 2.25-2.40 (1H, m, Proβ-H$_A$H$_B$), 3.54 (2H, t, J6.6, Proδ-H$_2$), 3.89 (1H, dd, J 17.1 and 3.9, Glyα-H$_A$H$_B$), 4.04 (1H, dd, J 17.2 and 5.3, Glyα-H$_A$H$_B$), 5.11 (2H, s, OCH$_2$Ph), 5.84 (1H, br t, J 4.2, N—H), 7.22-7.43 (5H, m, Ph) and 7.89 (1H, br s, —COOH); δ$_C$ (75 MHz; CDCl$_3$) 21.3 (CH$_3$, Proα-CH$_3$), 23.8 (CH$_2$, Proγ-C), 38.2 (CH$_2$, Proβ-C), 43.6 (CH$_2$, Glyα-C), 47.2 (CH$_2$, Proδ-C), 66.7 (quat, Proα-C), 66.8 (CH$_2$, OCH$_2$Ph), 127.9 (CH, Ph), 127.9 (CH, Ph), 128.4, (CH, Ph), 136.4 (quat., Ph), 156.4 (quat., NCO$_2$), 167.5 (quat., Gly-CON) and 176.7 (quat., CO); m/z (EI+) 320.1368 (M$^+$. C$_{16}$H$_{20}$N$_2$O$_5$ requires 320.1372).

Dibenzyl N-benzyloxycarbonyl-glycyl-L-2-methyl-prolyl-L-glutamate 7

Triethylamine (0.50 cm$^3$, 3.59 mmol) was added dropwise to a solution of dipeptide 5 (0.36 g, 1.12 mmol) and L-glutamic acid dibenzyl ester p-toluenesulphonate 6 (0.73 g, 1.46 mmol) in methylene chloride (60 cm$^3$) under nitrogen at room temperature, and the reaction mixture stirred for 10 min. Bis(2-oxo-3-oxazolidinyl)phosphinic chloride (BoPCl, 97%) (0.37 g, 1.41 mmol) was added and the colourless solution stirred for 17 h. The methylene chloride solution was washed successively with 10% aqueous hydrochloric acid (50 cm$^3$) and saturated aqueous sodium hydrogen carbonate (50 cm$^3$), dried (MgSO$_4$), filtered, and evaporated to dryness in vacuo. Purification of the resultant residue by repeated (2×) flash column chromatography (24 g SiO$_2$; 30-70% ethyl acetate-hexane; gradient elution) yielded fully protected tripeptide 7 (0.63 g, 89%) as a colourless oil. Tripeptide 7 was shown to be exclusively the trans-orientated conformer by NMR analysis: R$_f$ 0.55 (EtOAc); [α]$_D$ −41.9 (c 0.29 in CH$_2$Cl$_2$); ν$_{max}$ (film)/cm$^{-1}$ 3583, 3353 br, 2950, 1734, 1660, 1521, 1499, 1454, 1429, 1257, 1214, 1188, 1166, 1051, 911, 737 and 697; (400 MHz; CDCl$_3$; Me$_4$Si) 1.64 (3H, s, Proα-CH$_3$), 1.72 (1H, dt, J 12.8, 7.6 and 7.6, Proβ-H$_A$H$_B$), 1.92 (2H, 5 lines, J 6.7, Proγ-H$_2$), 2.04 (1H, 6 lines, J 7.3 Gluβ-H$_A$H$_B$), 2.17-2.27 (1H, m, Gluβ-H$_A$H$_B$), 2.35-2.51 (3H, m, Proβ-H$_A$H$_B$ and Gluγ-H$_2$), 3.37-3.57 (2H, m, Proδ-H$_2$), 3.90 (1H, dd, J 17.0 and 3.6, Glyα-H$_A$H$_B$), 4.00 (1H, dd, J 17.1 and 5.1, Glyα-H$_A$H$_B$), 4.56 (1H, td, J 7.7 and 4.9, Gluα-H), 5.05-5.20 (6H, m, 3×OCH$_2$Ph), 5.66-5.72 (1H, br m, Gly-NH), 7.26-7.37 (15H, m, 3×Ph) and 7.44 (1H, d, J 7.2, Glu-NH); δ$_C$ (100 MHz; CDCl$_3$) 21.9 (CH$_3$, Proα-CH$_3$), 23.4 (CH$_2$, Proγ-C), 26.6 (CH$_2$, Gluβ-C), 30.1 (CH$_2$, Gluγ-C), 38.3 (CH$_2$, Proβ-C), 43.9 (CH$_2$, Glyα-C), 47.6 (CH$_2$, Proδ-C), 52.2 (CH, Gluα-C), 66.4 (CH$_2$, OCH$_2$Ph), 66.8 (CH$_2$, OCH$_2$Ph), 67.1 (CH$_2$, OCH$_2$Ph), 68.2 (quat, Proα-C), 127.9 (CH, Ph), 128.0 (CH, Ph), 128.1, (CH, Ph), 128.2, (CH, Ph), 128.2, (CH, Ph), 128.3, (CH, Ph), 128.4, (CH, Ph), 128.5, (CH, Ph), 128.5, (CH, Ph), 135.2 (quat., Ph), 135.7 (quat., Ph), 136.4 (quat., Ph), 156.1 (quat., NCO$_2$), 167.3 (quat., Gly-CO), 171.4 (quat., CO), 172.9 (quat., CO) and 173.4 (quat., CO); m/z (FAB+) 630.2809 (MH$^+$. C$_{35}$H$_{40}$N$_3$O$_8$ requires 630.2815).

Glycyl-L-2-methylprolyl-L-glutamic acid (G-2MePE)

A mixture of the protected tripeptide 7 (0.63 g, 1.00 mmol) and 10 wt. % palladium on activated carbon (0.32 g, 0.30 mmol) in 91:9 methanol-water (22 cm$^3$) was stirred under an atmosphere of hydrogen at room temperature, protected from light, for 23 h. The reaction mixture was filtered through a Celite™ pad and the pad washed with 75:25 methanol-water (200 cm$^3$). The filtrate was concentrated to dryness under reduced pressure and the residue triturated with anhydrous diethyl ether to afford a 38:1 mixture of G-2MePE and tentatively methylamine 8 (0.27 g, 86%) as an extremely hygroscopic white solid. Analytical reverse-phase HPLC studies on the mixture (Altech Econosphere C$_{18}$ Si column, 150×4.6 mm, 5 µm; 5 min flush with H$_2$O (0.05% TFA) then steady gradient over 25 min to MeCN as eluent at flow rate of 1 ml/min; detection using diode array] indicated it was a 38:1 mixture of two eluting peaks with retention times of 13.64 and 14.44 min at 207 and 197 nm, respectively. G-2MePE was shown to be a 73:27 trans:cis mixture of conformers by $^1$H NMR analysis (the ratio was estimated from the relative intensities of the double doublet and triplet at δ 4.18 and 3.71, assigned to the Gluα-H protons of the major and minor conformers, respectively): mp 144° C.$^Φ$; [α]$_D$ −52.4 (c 0.19 in H$_2$O); δ$_H$ (300 MHz; D$_2$O; internal MeOH) 1.52 (3H, s, Proα-CH$_3$), 1.81-2.21 (6H, m, Proβ-H$_2$, Proγ-H$_2$ and Gluβ-H$_2$), 2.34 (1.46H, t, J 7.2, Gluγ-H$_2$), 2.42* (0.54H, t, J 7.3, Gluγ-H$_2$), 3.50-3.66 (2H, m, Proδ-H$_2$), 3.71* (0.27H, t, J 6.2, Gluα-H), 3.85 (1H, d, J 16.6, Glyα-H$_A$H$_B$), 3.92 (1H, d, J 16.6, Glyα-H$_A$H$_B$) and 4.18 (0.73H, dd, J 8.4 and 4.7, Gluα-H); δ$_C$ (75 MHz; D$_2$O; internal MeOH) 21.8 (CH$_3$, Proα-CH$_3$), 25.0 (CH$_2$, Proγ-C), 27.8* (CH$_2$, Gluβ-C), 28.8 (CH$_2$, Gluβ-C), 32.9 (CH$_2$, Gluγ-C), 40.8 (CH$_2$, Proβ-C), 42.7 (CH$_2$, Glyα-C), 49.5 (CH$_2$, Proδ-C), 56.0* (CH, Gluoα-C), 56.4 (CH, Gluα-C), 69.8 (quat, Proα-C), 166.5 (quat., Gly-CO), 177.3 (quat., Pro-CON), 179.2 (quat., Gluα-CO), 180.2* (quat., Gluγ-CO) and 180.6 (quat., Gluγ-CO); m/z (FAB+) 316.1508 (MH$^+$. C$_{13}$H$_{22}$N$_3$O$_6$ requires 316.1509).

Example 3

Effects of G-2MePE on Animals with Middle Cerebral Artery Occlusion-I

To determine whether G-2MePE might be a suitable therapeutic with applications for treating stroke, we carried out a series of studies in an art-recognized model of stroke in rats, namely, middle coronary artery occlusion (MCAO). This system is known to mimic neurological and behavioural signs and symptoms of stroke in humans, and therefore, the results obtained are predictive of therapeutic effects in humans with strokes. We measured infarct size, and the appearance of GFAP-positive astrocytes and microglial cell activation, both of which are recognized in the art as being indicators of brain damage. Thus, results obtained using GFAP and microglial cell activation are indicative of stroke in human beings and reductions in GFAP staining and microglial cell activation are predictive of therapeutic effects in humans suffering from stroke.

Materials and Methods

Endothelin-1 Induced Middle Cerebral Artery Occlusion

All surgical and experimental procedures carried out in this study had been approved by the University of Auckland Animal Ethics Committee. All efforts were made to minimise any animal suffering and the number of animals used. Adult male Sprague-Dawley rats (280-350 g) were used.

An inhalation anaesthetic (halothane) was co-administered with oxygen to anaesthetise the rats. Initially 5% halothane/oxygen was applied to anaesthetise the animal, and then 2.5% halothane was used to maintain the anaesthesia. Once under anaesthesia, a guide cannula was implanted on the skull of the anaesthetized rats, which was fixed into position with dental cement. Following this implantation, the jugular vein of the animal was also cannulated. Three days post cannula implantation and cannulation, the rats were anaesthetized again as above and subjected to MCA occlusion according to the method of Sharkey and co-workers (Sharkey et al., 1993). This involved placing the head of each rat on a stereotaxic frame and locking it into position. The animals were also placed on a heating pad, which is designed to maintain body temperature within the physiological range for the duration of the surgical procedure.

The hair over the scalp was clipped short with a pair of scissors, sponged and wiped dry with a solution of Betadine® (iodine). Following this, a midline skin incision was made through the scalp to expose the coronal suture line (bregma) of the skull prior to a small opening being drilled through the cranial bone using the following co-ordinates 0.2 mm anterior to and 5.2 mm lateral to bregma. Through the guide cannula, a 28-gauge infusion needle that was connected to a 10 µl syringe containing 100 pmol of porcine endothelin-1 (Et-1; Sigma-Aldrich Inc., Saint Louis, Mo., USA) in 3 µl of saline was vertically inserted to a depth of 8.7 mm below the surface of the skull. At a delivery rate of 1 µl per minute, a total volume of 3 µl of solution was manually infused over the period of three minutes. With the completion of the infusion, the needle was left in place for five more minutes before being withdrawn from the brain whilst the skin incision was sutured and the animals moved to a warmed incubator (37° C.) in order to recover from the surgery. Once awake, the animals were then transferred to their cages where they had full access to both food and water.

GPE and G-2MePE Treatment

At five hours post Et-1 (100 pmol) injection, GPE (3 mg/kg/h) (Bachem AG, Basal, Switzerland) or succinate buffer (vehicle treated group) in the first study and G-2MePE (0.3 mg/kg/h) (Neuren Pharmaceuticals Ltd, New Zealand) or succinate buffer (vehicle treated group) in the second study was continuously infused i.v. into the animal via the jugular vein cannula at a delivery rate of 0.5 ml/h for four hours.

Histological Procedures

Five days following the drug treatment, the animals were sacrificed using an overdose of sodium pentobarbital and the brains collected for histological evaluation of neuronal survival. The rats were perfused transcardially with 0.9% normal saline followed by 10% formalin. The brain was removed from the skull and stored in the same fixative solution for at least 24 hours. Three 2 mm coronal sections using a rodent brain matrix (RBM-3000C/RBM-4000C, ASI Instruments, USA) were cut. Section A: directly in front of the optical chiasma, section B: directly following section A posterior to the optical chiasma and section C directly following section B. The slices were held in 10% formalin for at least 24 hours, processed in increasing percentage of alcohol and in chloroform and embedded in paraffin for further cutting. At a thickness of 8 µm, coronal sections were cut on a Leica® microtome (Leica Instruments, Nussloch, Germany), mounted onto Polysine™ microscope coated slides (BioLab Scientific, NZ) and stained with thionin-acid fuchsin prior to microscopic evaluation.

Immunohistochemistry

Eight-micron thickness paraffin-embedded sections were mounted to microscope slides, dewaxed in xylene and brought up to water through the standard graded ethanol procedure. These slides were then washed three times for five minutes (3×5 min) in 0.1M phosphate buffered saline (PBS), before being transferred to a solution of 1% H$_2$O$_2$ in absolute methanol for 30 minutes at room temperature in order to block for endogenous peroxidases. Following another conventional wash, non-specific protein binding was blocked with 2% normal horse serum (NHS) (Vector Laboratories Inc., Burlingame, Calif., USA) in 0.1M PBS at room temperature for an hour. After this time period, the NHS was drained away carefully and the respective primary antibodies were loaded onto the sections.

For astrocytic immunostaining, glial fibrillary acidic protein (GFAP) was used as a marker. These sections were incubated with a primary monoclonal anti-GFAP (Sigma-Aldrich Inc., Saint Louis, Mo., USA) antibody from mouse at a dilution of 1:1000 in 0.1M PBS containing 2% NHS overnight at 4° C. in a humidified chamber. The primary antibody was washed off the next day with 0.1M PBS (3×5 min) and the section was incubated with horse-anti-mouse biotinylated secondary antibody (1:200, Vector Laboratories Inc., Burlingame, Calif., USA) in 0.1M PBS plus 2% NHS overnight at 4° C. in a humidified chamber. The antibody was washed off the following day and the section incubated with ExtrAvidin peroxidase conjugate (1:500, Sigma) in 0.1M PBS plus 2% NHS at room temperature. After three hours, the slides were washed and developed with DAB for the required time until a brown reaction product was observed.

For microglial immunostaining, isolectin $B_4$ peroxidase labelled from *Bandeiraea simplicifolia* (Sigma-Aldrich Inc., Saint Louis, Mo., USA) was used as a marker. With the only exception of using 0.1M Tris-buffered saline (TBS) plus 0.2% triton as opposed to 0.1M PBS, these sections went through the exact similar protocol to that required for immunolabelling of GFAP. However, in this assay, there was no blocking for non-specific protein binding. Therefore, following the blocking for endogenous peroxidases step, a standard wash (3×5 min) in TBS plus 0.2% triton was carried out prior to the sections being loaded with reconstituted isolectin $B_4$ (10 μg/ml). The slides were incubated overnight at 4° C. in a humidified chamber. After 24 hours, the isolectin $B_4$ was washed off and sections developed with DAB for the required time until a brown reaction product was noticeable.

The time required for DAB colour development was controlled to be equal for all sections within both studies. Following DAB colour development, the stained sections were dehydrated through the standard increasing ethanol gradient and xylene procedure. Finally the slides were quickly allowed to air dry, mounted using DPX mounting medium and cover-slipped.

Image Analysis

Slides were visualised under bright-field illumination and the extent of neuronal damage, as well as the astrocytic and microglial responses were analysed on a Carl Zeiss Axioskope™ microscope using AxioVision™ software (AxioVision 3.0, Carl Zeiss Software, Hallbergmoos, Germany). For analysis of GFAP immunohistochemistry, the area of total GFAP immunostaining in the peri-infarct zone was calculated in mm² and converted into a percentage against the total area (in mm²) of the ipsilateral (injured) hemisphere, whilst for isolectin $B_4$, the microglial immunopositive cells were counted in three screen fields (×10 magnification) and then averaged. Also, in every experiment, a control section with no primary antibody was used as a negative control. Furthermore, the histology and immunohistochemistry was analysed by an individual blinded to the treatment groups.

Statistical Analysis

Student t-test was used for comparing the treatment effects of GPE and G-2MePE to its vehicle groups, respectively. All statistical calculations were carried out using GraphPad Prism™ software (Version 3.02, GraphPad Software Inc., San Diego, Calif., USA). Data are presented as mean±S.E.M. and significance was defined at p<0.05.

Results

Effect of GPE and G-2MePE on Infarct Size

Figure 12:
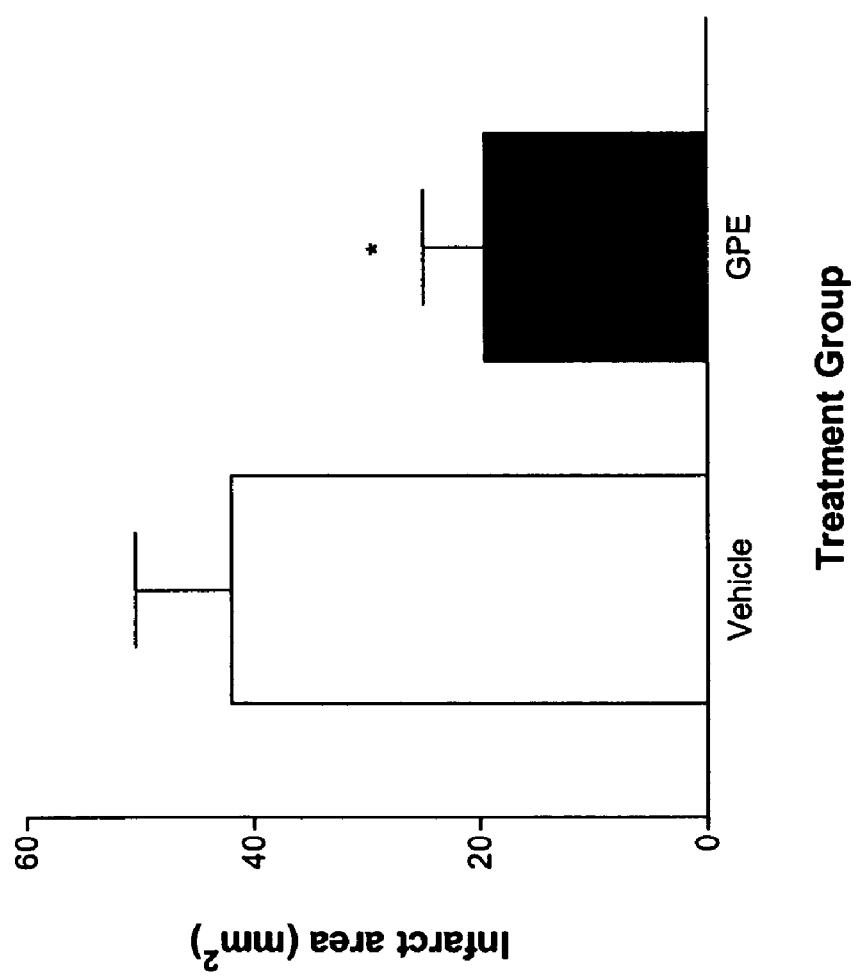
FIG. 12 shows the effect of delayed administration of GPE or vehicle treatment on area of infarct (in $mm^2$) following an Et-1 MCAO model. Five hours post Et-1 injection, GPE-treated (3 mg/kg/h) (■, n=15) or vehicle-treated (succinate buffer) (□, n=14) animals were continuously infused i.v. via the jugular vein at 0.5 ml/h for four hours. Data are presented as mean±S.E.M. and significance was defined at $p<0.05$.
Figure 13:
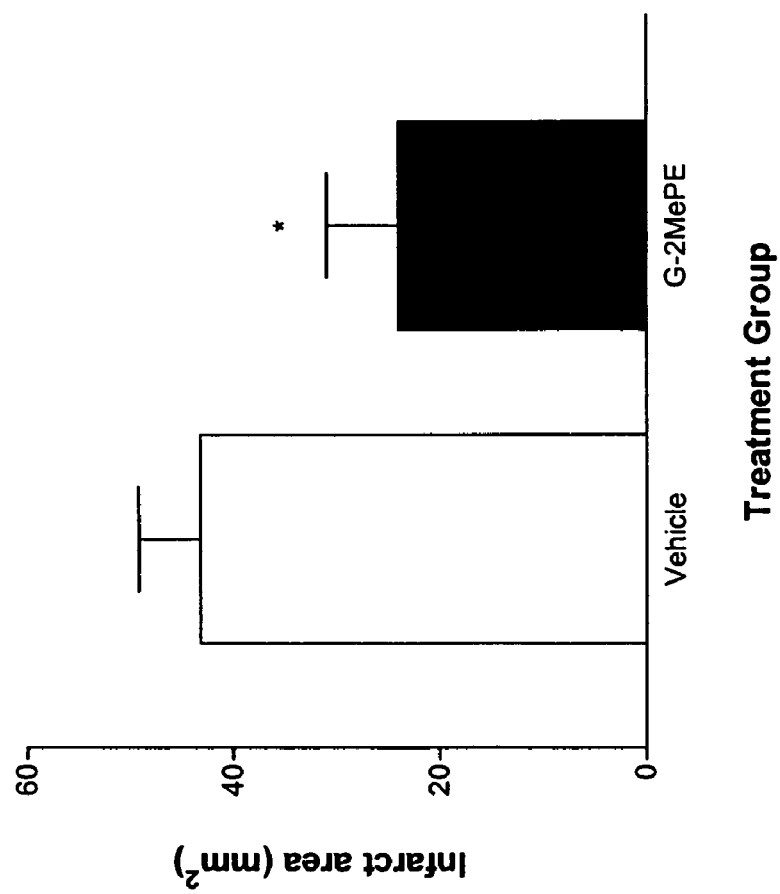
FIG. 13 shows the effect of delayed administration of G-2MePE or vehicle treatment on area of infarct (in $mm^2$) following an Et-1 MCAO model. Five hours post Et-1 injection, G-2MePE-treated (0.3 mg/kg/h) (■, n=14) or vehicle-treated (succinate buffer) (□, n=13) animals were continuously infused i.v. via the jugular vein at 0.5 ml/h for four hours. Data are presented as mean±S.E.M. and significance was defined at $p<0.05$.

In the GPE study, the area of infarct in animals treated with vehicle was 42.0±8.4 mm² (n=14, FIG. 12). Treatment with GPE (3 mg/kg/h) significantly reduced the area of the infarct to 19.6±5.4 mm² when compared to its vehicle treated group (n=15, *P<0.05). By contrast, in the G-2MePE study, animals treated with vehicle had an area of infarct of 43.2±6.0 mm² (n=13, FIG. 13). Treatment with G-2MePE (0.3 mg/kg/h) significantly reduced the area of the infarct to 24.0±7.0 mm² as opposed to its vehicle treated group (n=14, *P<0.05).

GFAP Immunostaining

Figure 14:
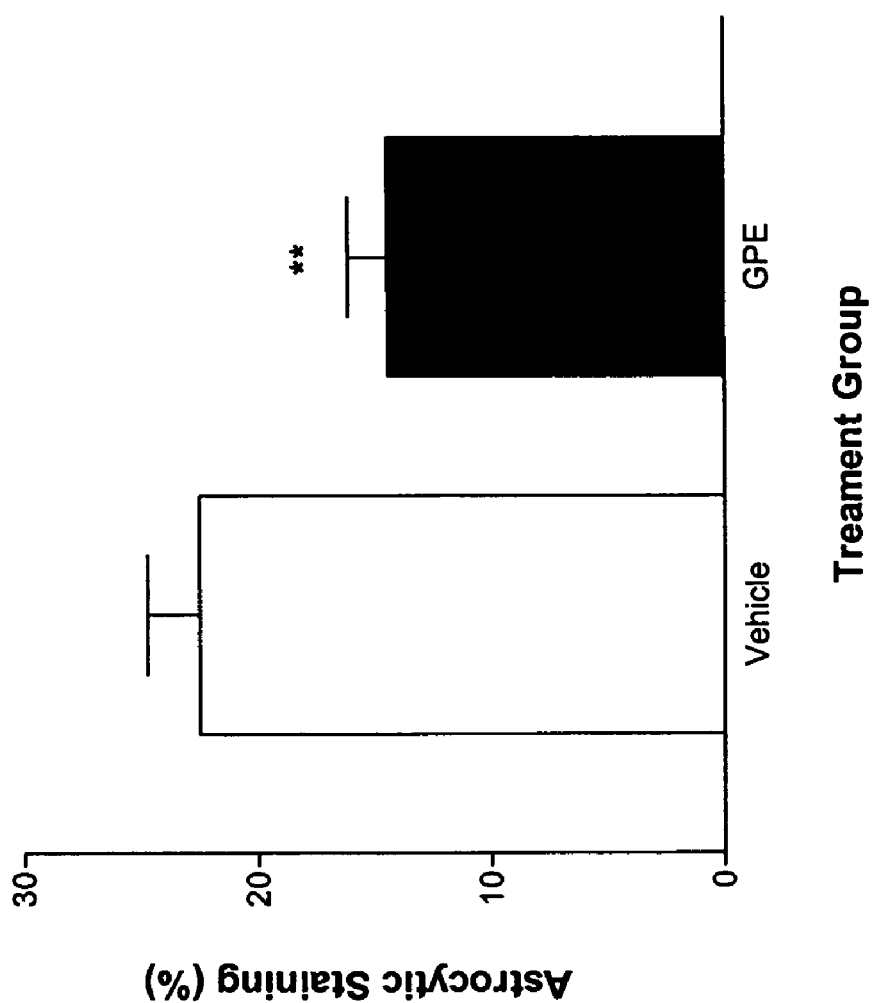
FIG. 14 shows the effect of delayed administration of GPE or vehicle treatment on GFAP staining (as a percentage) following an Et-1 MCAO model. Five hours post Et-1 injection, GPE-treated (3 mg/kg/h) (■, n=10) or vehicle-treated (succinate buffer) (□, n=10) animals were continuously infused i.v. via the jugular vein at 0.5 ml/h for four hours. Data are presented as mean±S.E.M. and significance was defined at $p<0.01$.
Figure 15:
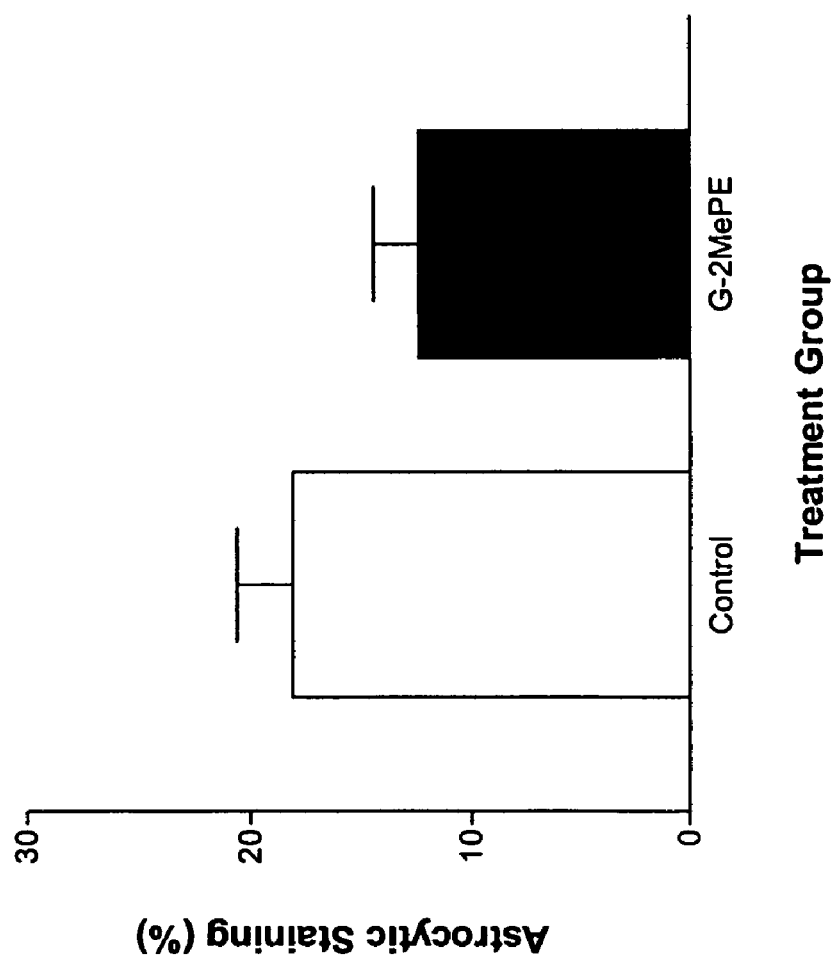
FIG. 15 shows the effect of delayed administration of G-2MePE or vehicle treatment on GFAP staining (as a percentage) following an Et-1 MCAO model. Five hours post Et-1 injection, G-2MePE-treated (0.3 mg/kg/h) (■, n=10) or vehicle-treated (succinate buffer) (□, n=10) animals were continuously infused i.v. via the jugular vein at 0.5 ml/h for four hours. Data are presented as mean±S.E.M.

The astrocytic (GFAP positive cells) response following Et-1 induced MCA occlusion was determined in both studies. There was a significant reduction in the area of GFAP immunostaining after GPE treatment (14.5±1.7%, n=10, **P<0.01) when compared with to its vehicle treated group (22.5±2.2%, n=10, FIG. 14). However, treatment with G-2MePE revealed only a strong inhibitory trend in GFAP immunostaining as opposed to its vehicle treated group (12.4±2.0% vs. 18.1±2.5% for the control group, n=10, FIG. 15).

Microglia Immunostaining

Figure 16:
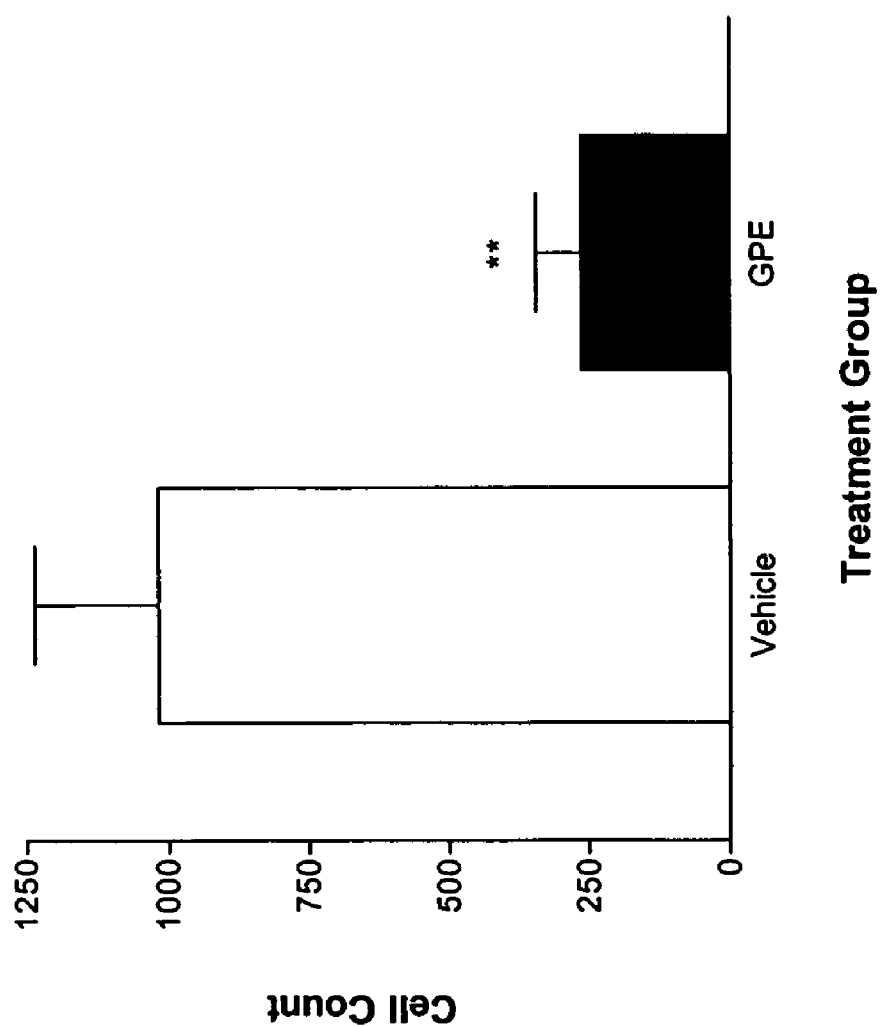
FIG. 16 shows the effect of delayed administration of GPE or vehicle treatment on microglial activation (cell count) following an Et-1 MCAO model. Five hours post Et-1 injection, GPE-treated (3 mg/kg/h) (■, n=10) or vehicle-treated (succinate buffer) (□, n=10) animals were continuously infused i.v. via the jugular vein at 0.5 ml/h for four hours. Data are presented as mean±S.E.M. and significance was defined at $p<0.01$.
Figure 17:
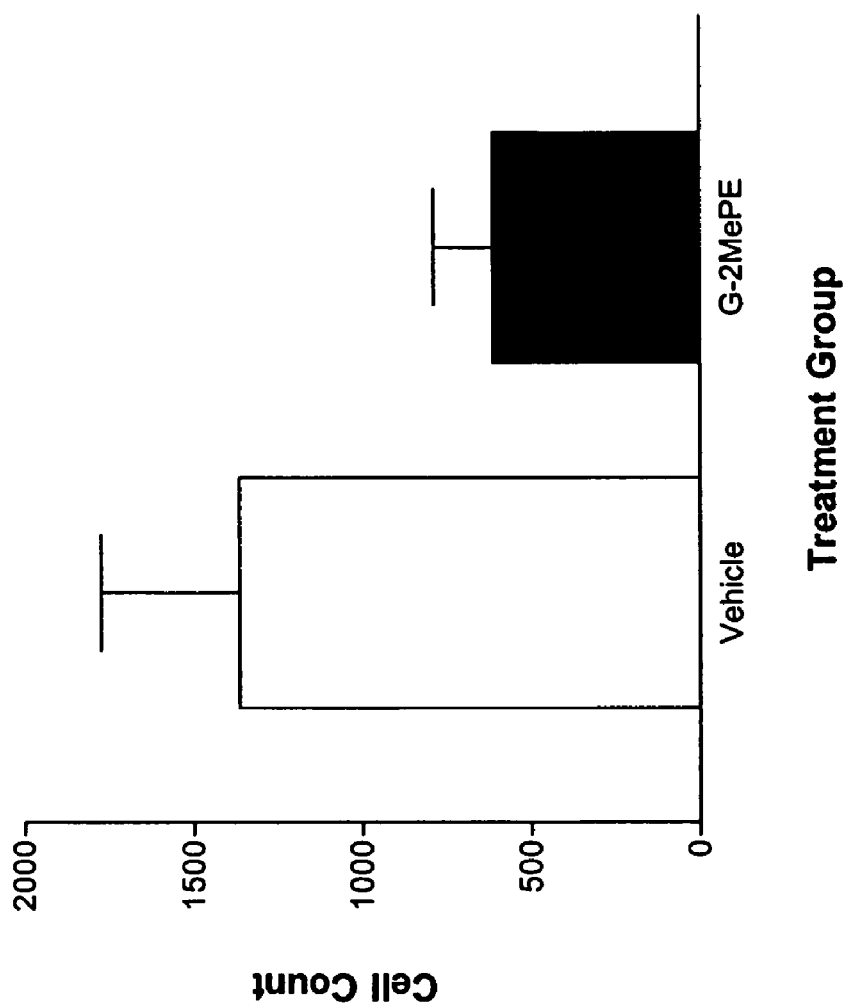
FIG. 17 shows the effect of delayed administration of G-2MePE or vehicle treatment on microglial activation (cell count) following an Et-1 MCAO model. Five hours post Et-1 injection, G-2MePE-treated (0.3 mg/kg/h) (■, n=10) or vehicle-treated (succinate buffer) (□, n=10) animals were continuously infused i.v. via the jugular vein at 0.5 ml/h for four hours. Data are presented as mean±S.E.M.

The response of microglia (isolectin $B_4$ positive cells) was investigated. The number of microglial immunopositive cells showed a significant (**P<0.01) decrease (264±81 vs. 1019±217 for the vehicle treated group) after GPE treatment (n=10, FIG. 16). G-2MePE treated animals (n=10, FIG. 17) also showed a reduction in the number of microglial immunopositive cells as opposed to the vehicle treated group (612.2±174.6 vs. 1367±409.0 for the vehicle group) although this difference did not reach statistical significance.

Conclusions

GPE and G-2MePE exhibited strong neuroprotective actions following continuous i.v. infusion in adult male rats subsequent to an Et-1 induced MCA occlusion in a model of cerebral ischaemia. Interestingly, the neuroprotective effects of both these compounds were evident when administered at a time point of 5-9 h after focal cerebral ischaemia demonstrating a wide window of therapeutic opportunity. These neuroprotective effects may be related to an inhibition of both astrocytic and microglial activation following cerebral ischaemia. We conclude from these studies that both GPE and G-2MePE can be effective therapeutic agents useful in treating animals with middle cerebral artery occlusion. We further conclude that because the effects were observed in an animal system in vivo, in an art-recognized animal system that is predictive of effects in humans with stroke, that both GPE and G-2MePE can be effective in treating humans with stroke or other hypoxic or ischemic injury of the brain.

Example 4

Neuroprotective effects G-2MePE in a Penetrating Ballistic Brain Injury-I

To determine whether G-2MePE might be a useful therapeutic agent in treating brain injury, we carried out a series of studies in rats that had received penetrating ballistic brain injury (PBBI) that mimics the types of injuries experienced by humans. In particular, behavioural tests of rats subjected to PBBI are useful in determining neurological deficits that commonly occur with such injuries.

Introduction

The rat penetrating ballistic brain injury (PBBI) paradigm models head injury caused by a high-energy bullet wound. It is a severe model of traumatic brain injury and has been characterised by using neurological, physiological and histopathological outcomes (Williams et al. Journal of Neurotrauma. 2005: 22(2); pp. 314-332), herein expressly incorporated fully by reference. G-2MePE was evaluated in the PBBI model to investigate its effect on post-injury locomotor skills, defined by the competence of post-injury rats to traverse an elevated walking beam.

PBBI Method

Sprague-Dawley rats were anaesthetised (induced with 5% isoflurane, maintained with 2% isoflurane) for surgery and placed in a stereotaxic device to enable an accurate and reproducible injury. A small burr hole was drilled in the skull to expose the right frontal pole (+4.5 mm AP, +2 mm medial; relative to Bregma) and additional bone was removed 1 mm anterior to the burr hole to enable insertion of the PBBI probe. The probe was mounted to the arm of the stereotaxic frame, at 50° from vertical and 25° counter-clockwise from the midline.

The PBBI insult in this paradigm is designed to model the immediate tract caused by a 7.62 mm high velocity round, as well as the cavity that forms in the tract by energy dissipation from the missile. To achieve this, the probe was lowered to 12 mm depth from dura and the balloon that covers the probe expanded with a sudden inflation of air to create the cavity injury. The inflation/deflation lasts no more than 10-20 ms. After induction of the injury the probe was removed and the skull resealed with bone wax, and the scalp wound sutured.

Thirty minutes following injury, rats were given either saline control or G-2MePE delivered by intravenous infusion for 4 or 12 hours.

Rats were allowed a recovery period of 72 hours post surgery prior to behavioural testing. For behavioural testing rats were placed on an elevated walking beam, and their capacity to traverse the beam was assessed. Automatic tracking of foot-faults occurring when the rats walked along the beam were recorded. In addition, rats were scored for severity of clinical signs (neurobehavioural dysfunction) and post-mortem for injury size following the PBBI (H&E staining) and activated microglia cell counts (OX-18 staining).

Results

The effects of G-2MePE administered i.v. for 4 h (0, 0.3, 3 mg/kg/h) on foot-faults and neurological disability score were tested at 24 h and 72 h following PBBI.

Figure 18A:
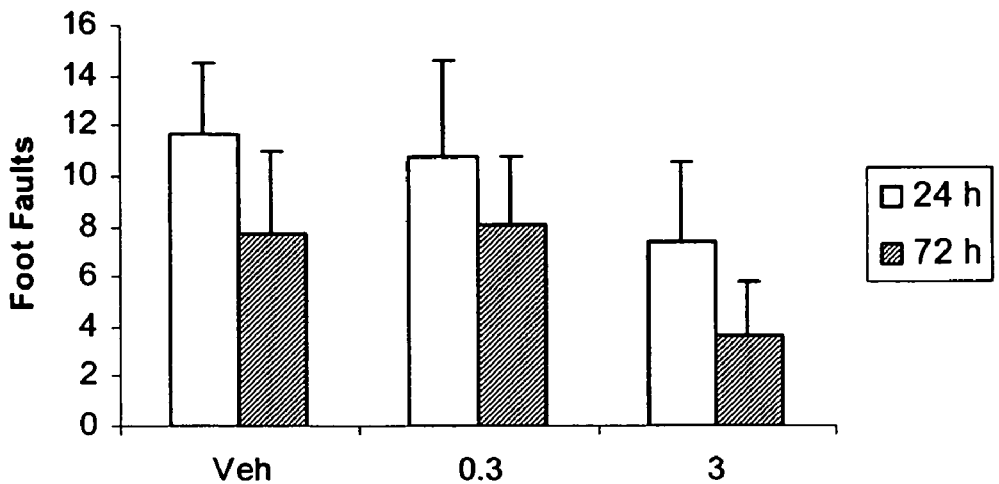
FIG. 18 shows the effect of G-2MePE administered i.v 30 minutes post-PBBI (0, 0.3, 3 mg/kg/h×4 h) on balance beam performance (FIG. 18A) and neurological disability score (FIG. 18B), tested 24 h and 72 h following penetrating ballistic brain injury (PBBI).
Figure 18B:
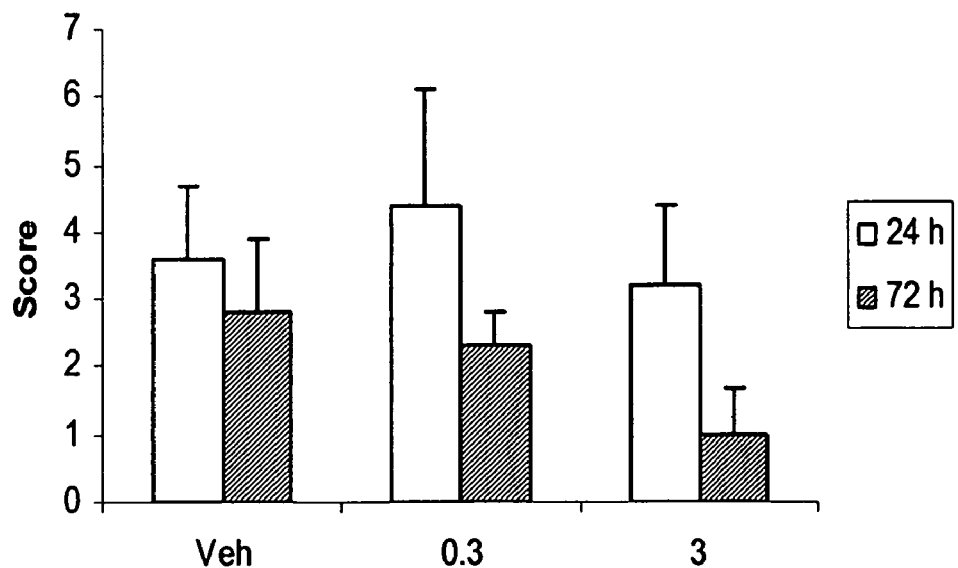

Foot-fault count was 54% lower and neurological disability score was 69% lower, in rats administered 3 mg/kg/h×4 h G-2MePE when tested 72 h post-injury (FIGS. 18A and 18B respectively).

Figure 19:
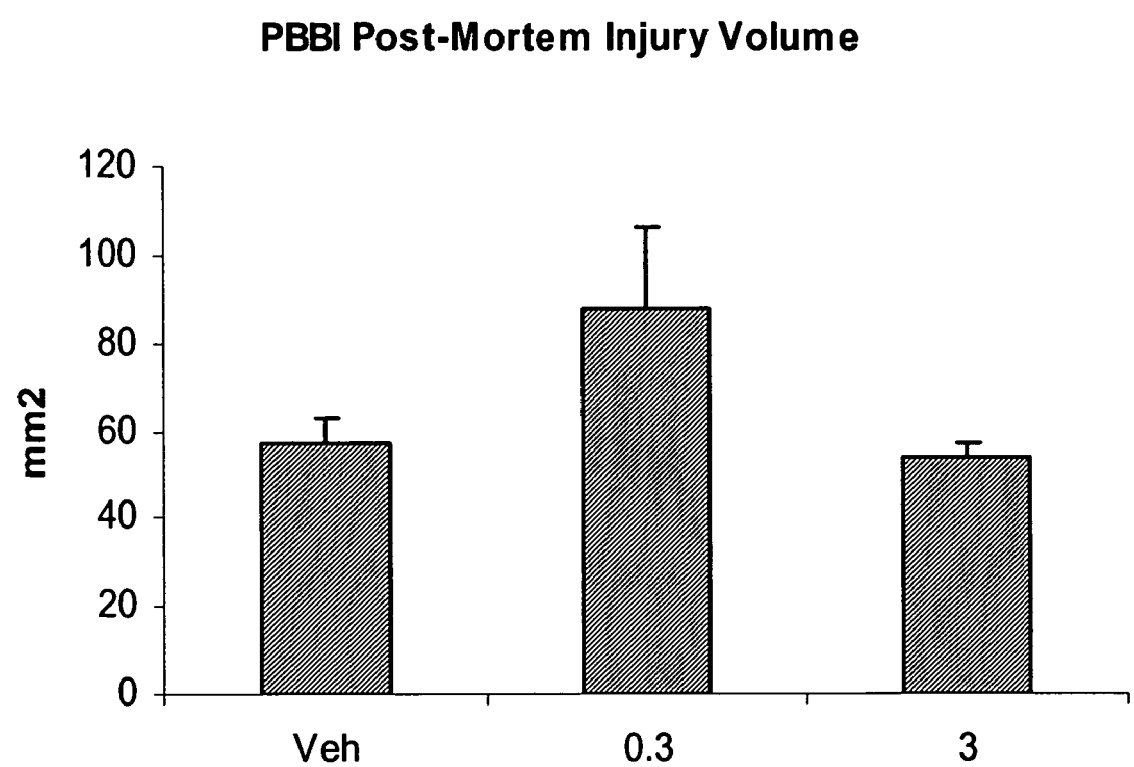
FIG. 19 shows the effect of G-2MePE administered i.v. 30 minutes post-PBBI (0, 0.3, 3 mg/kg/h×4 h) on total injury volume to the brain assessed post-mortem following PBBI insult.

No significant effect of G-2MePE administered i.v. (0, 0.3, 3 mg/kg/h) on total injury volume to the brain assessed post-mortem following PBBI insult was observed (FIG. 19).

Figure 20:
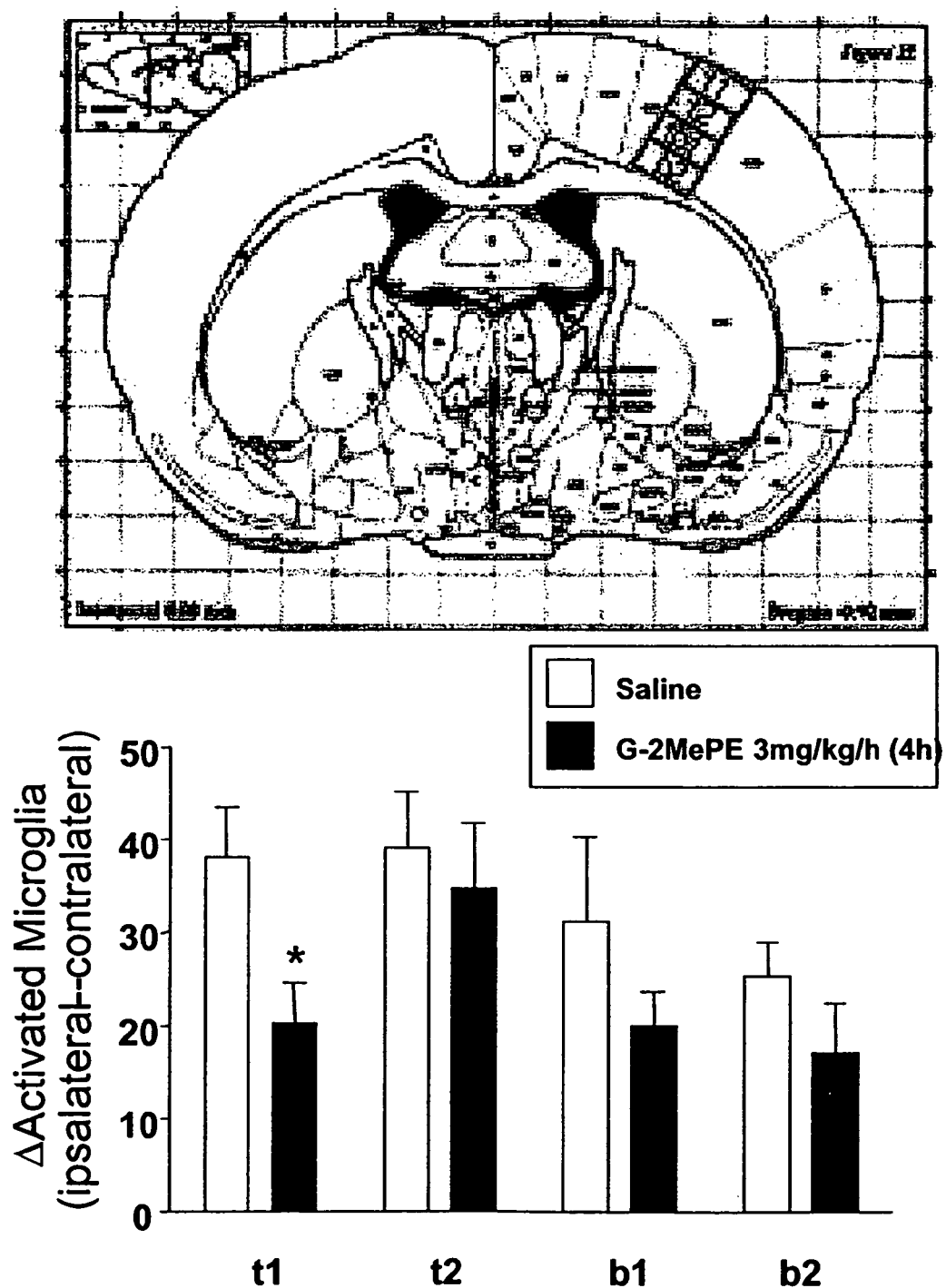
FIG. 20 shows the effect of G-2MePE (administered i.v; 3.0 mg/kg/h; 4 h infusion) 30 min post-PBBI on the activation of microglia, measured by OX-18 staining.

The effect of G-2MePE (3.0 mg/kg/h; administered i.v. as a 4 h infusion commencing 30 min post-PBBI) on the activation of microglia were measured by OX-18 staining (FIG. 20). Microglia activation in area t1 was significantly reduced in the G-2MePE-treated group, and in areas t2, b1 and b2 a marked trend towards reduction of microglial activation was observed in all G-2MePE treated groups.

Experiment 2

In experiment 2 Rats were given either saline control or G-2MePE for 12 hours at either 0.01, 0.1, 1, 3, or 10 mg/kg/h, with infusion initiated 30 min post-PBBI insult.

Results

Figure 21A:
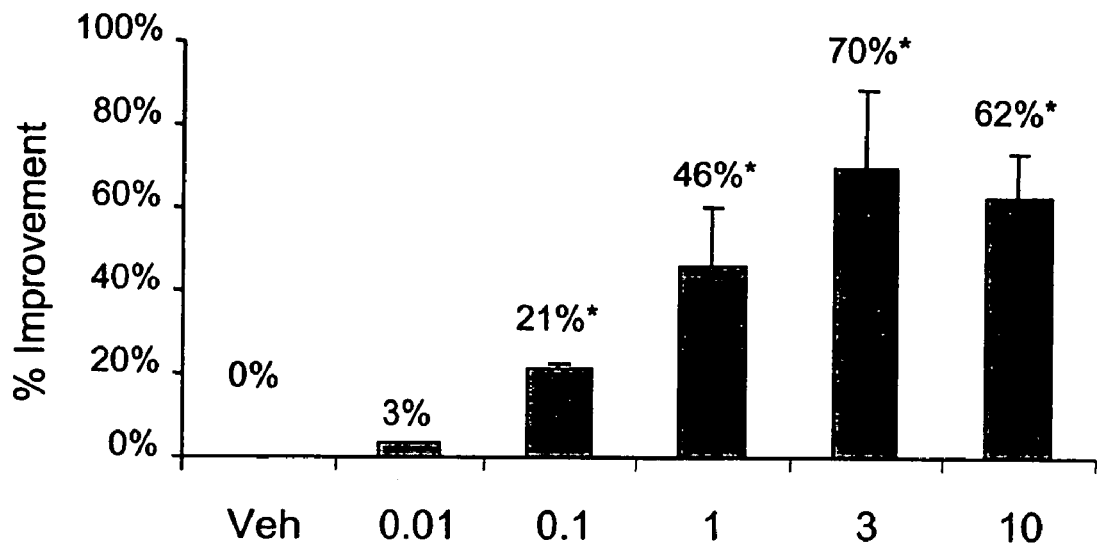
FIG. 21 (A). shows the dose response effect of G-2MePE administered i.v. (0, 0.01, 0.1, 1, 3, or 10 mg/kg/h×12 h) at 30 min post PBBI on balance beam performance. (B). shows the effect of G-2MePE administered i.v. (0, 1, 3, or 10 mg/kg/h× 12 h) at 30 min post PBBI on activation of injury induced microglia cells measured by OX-18 immunostaining.

With the exception of the 0.01 mg/kg dose, all other 12 hour infusion doses of G-2MePE significantly reduced foot-fault count measured at 72 h post surgery (* $p<0.05$, ANOVA with Bonferroni post-hoc test) (FIG. 21A). No statistically significant effects on neurological score or injury size (data not shown) were observed.

Figure 21B:
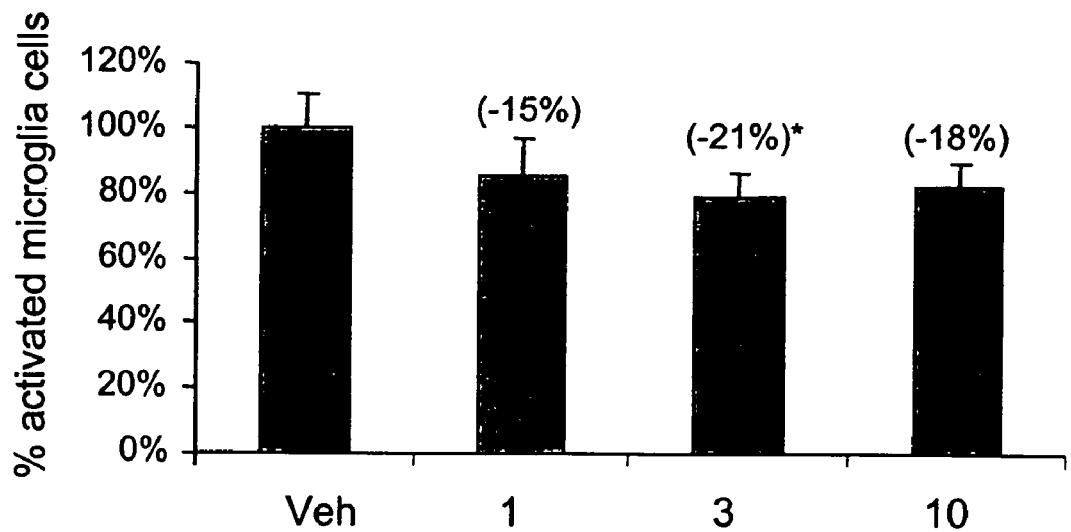

The effect of G-2MePE administered i.v. (0, 1, 3, or 10 mg/kg/h as a 12 h infusion beginning 30 min post PBBI) on the activation of microglia were measured by OX-18 immu-nostaing (FIG. 21B). Microglia activation in the area t1-b2 as a whole was significantly reduced in the G-2MePE (3 mg/kg/h×12 h) treated group and moderately reduced in the other two G-2MePE treated groups.

Conclusion

We conclude from these studies that G-2MePE is effective in reducing behavioural disorders associated with neural injury. Because the studies were in vivo studies in an art-recognized animal system for study of brain injury, these results are predictive of effects observed in humans with similar types of injuries. Therefore, we conclude that G-2MePE can be an effective therapeutic agent in treating people with penetrating brain injuries.

Example 5

Effects of G-2MePE on Non-Convulsive Seizures in Rats Following Middle-Cerebral Artery Occlusion Methods Animals Male Sprague-Dawley rats (270-330 g; Charles River Laboratories, Raleigh, Va.) were used in all of the following experiments. Food and water were provided ad libitum pre- and postsurgery, and the animals were individually housed under a 12-h light/dark cycle. For all surgical procedures, anesthesia was induced by 5% halothane and maintained at 2% isoflurane delivered in oxygen, and body temperatures were maintained normothermic ($37\pm1°$ C.) by means of a homeothermic heating system (Harvard Apparatus Inc., Holliston, Mass.). All procedures were approved by the Walter Reed Army Institute of Research Animal Care and Use Committee and all research was conducted in compliance with the Animal Welfare Act, Guide for the Care and Use of Laboratory Animals (National Research Council), and other federal statutes and regulations relating to animals and experiments involving animals. Animals were maintained in a facility accredited by the Association for Assessment and Accreditation of Laboratory Animal Care International.

Animal Preparation

Indwelling i.v. cannulas (polyethylene-50) were placed into the right jugular vein of all animals for drug delivery, and EEG electrodes were implanted in the skull (see below). Electrodes consisted of stainless steel screws (0-80×⅛ in.) soldered to insulated nichrome wire (0.2 mm in diameter). The screws were implanted epidurally and fixed to the skull using dental acrylate cement (Tortella et al., 1997). Free ends of the wires were soldered to a multi-pin connector (March Electronics, West Hempstead, N.Y.), also secured by dental acrylate.

Middle Cerebral Artery Occlusion (MCAo)

After 3 days of recovery from the above-mentioned procedures animals were subjected to permanent focal ischemia by using the filament method of MCAo as described previously (Tortella et al., 1999).

Anaesthesia was induced with 5% isoflurane delivered in oxygen and was maintained with 1.5% isoflurane throughout surgery. Briefly, the right external carotid artery was ligated, cauterised, and cut, and its branches were coagulated. A 35-mm length of 3-0 nylon monofilament with a rounded tip was then inserted into the internal carotid artery via the proximal end of the external carotid artery stump. The filament was advanced approximately 22 mm beyond the bifurcation of the internal and external carotid arteries, when slight resistance was encountered, thus permanently occluding the origin of the middle cerebral artery.

General Procedures

On the day of MCAo surgery, animals were transferred from their home cages to custom-designed Plexiglas EEG recording chambers (Dragonfly Inc., Ridgeley, W. Va.) equipped with multichannel gold contact swivel commutators (Plastics One, Roanoke, Va.). The multi-pin connector on the rat skull was connected to the swivel system via a flexible shielded cable, allowing free movement of the animals during recordings. The swivel commutators were interfaced with a digital EEG amplifier and recording system (Harmonie software; Astro-Med, West Warwick, R.I.). Baseline EEG signals were then recorded for 30 min before MCAo surgery and continuously throughout the 24-h ischemic period after surgery.

Treatment

Post-stroke rats were administered either saline (n=13) (1 mg/kg/h×12 h) or G-2MePE (n=10) administered as a 3.0 mg/kg bolus 30 min post MCAO immediately followed by 3 mg/kg/h infusion for 12 hours.

Evaluation of Neurological State

Neurological scoring (was performed before injury and 1 and 24 h post-MCAo using methods described in Tortella et al., J. Pharm. Exper. Therap. 291:399-408 (1999), expressly incorporated herein fully by reference. Animals not exhibiting maximal neurological deficit at 1 h post-occlusion were excluded from the study. Animals that died before the 24-h endpoint were not included in the main analyses of G-2MePE effects on NCS; drug and vehicle groups thus consisted of 13 (vehicle) and 10 (G-2MePE) surviving rats. Rectal temperatures were recorded before injury and 20 min, 1, 6, and 24 h post-occlusion. At 24 h, rats were deeply anesthetized, euthanized by decapitation, and brains were harvested for quantification of infarction.

EEG Recording and Analysis

Bipolar recordings were made from each cerebral hemisphere to monitor EEG activity. Two electrodes were positioned bilaterally over parietal cortices 5 mm lateral to midline, at 0 and 4 mm posterior to bregma, by procedures described above. A fifth reference electrode was implanted posterior to lambda over the transverse sinus/cerebellum.

Continuous EEG recordings were obtained for 24 h after injury and were reviewed in entirety at a display resolution of 1 mm/s for detection of electrographic seizures. Subsequently, all seizure events were verified at a recording speed of 30 mm/s for scoring of NCS episodes. Criteria for identifying NCS events were as follows: 1) the occurrence of repetitive spike, spike-and-wave, or sharp wave discharges recurring at frequencies >1 Hz, or continuous polyspiking; 2) spike amplitude greater than background activity; and 3) duration of continuous seizure activity (defined by 1 and 2) greater than 10 s. Seizures could be either generalized or focal, and consecutive seizure episodes were considered a single event if not separated by more than 10 s.

Based on the onset/offset times of each NCS event as defined by the above-mentioned criteria, several descriptive parameters were computed for each treatment group. NCS/rat and total duration of NCS were calculated as the mean value of all animals in each group. Average duration NCS and latency of onset were calculated as the mean values from only those animals exhibiting NCS in each group. EEG recordings were also visually evaluated for other EEG abnormalities, including depressed baseline amplitude, focal slowing, polymorphic delta activity, periodic lateralized epileptiform discharges, and interictal spikes, sharp waves, polyspikes, or spike/slow-wave complexes.

Figure 22A:
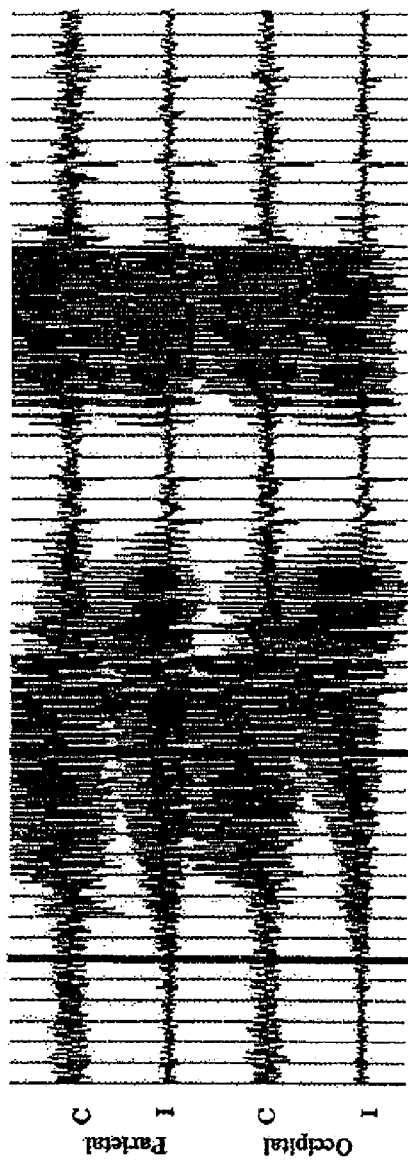
Figure 22B:
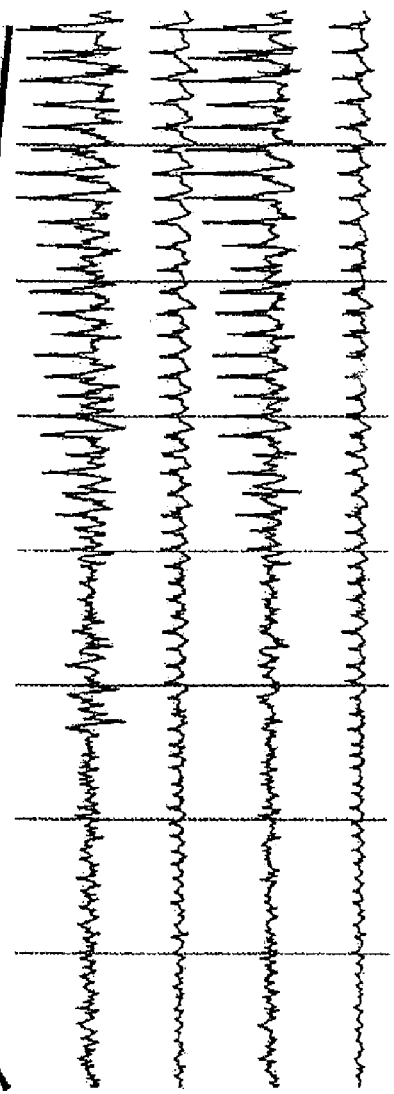
FIG. 22B shows a portion of the trace shown in FIG. 22A depicting rhythmic spike or sharp wave discharges with amplitudes increasing above baseline activity and developing into sustained, large-amplitude rhythmic spike, spike/wave, or polyspike discharges (FIG. 22B; right side). Vertical lines represent 3-second intervals.
Figure 22C:
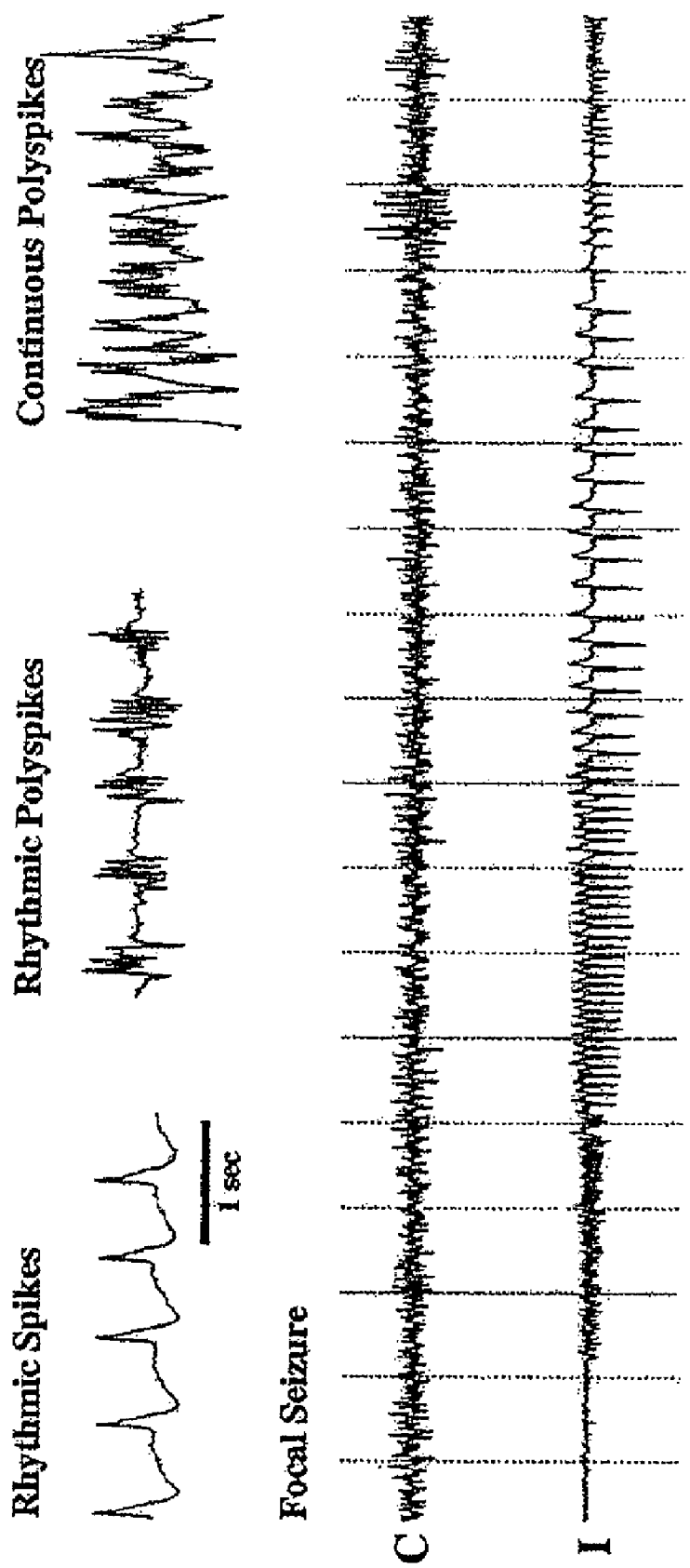
FIG. 22C (top traces) depict waveforms characteristic of NCS.
Figures 22D, 22E:
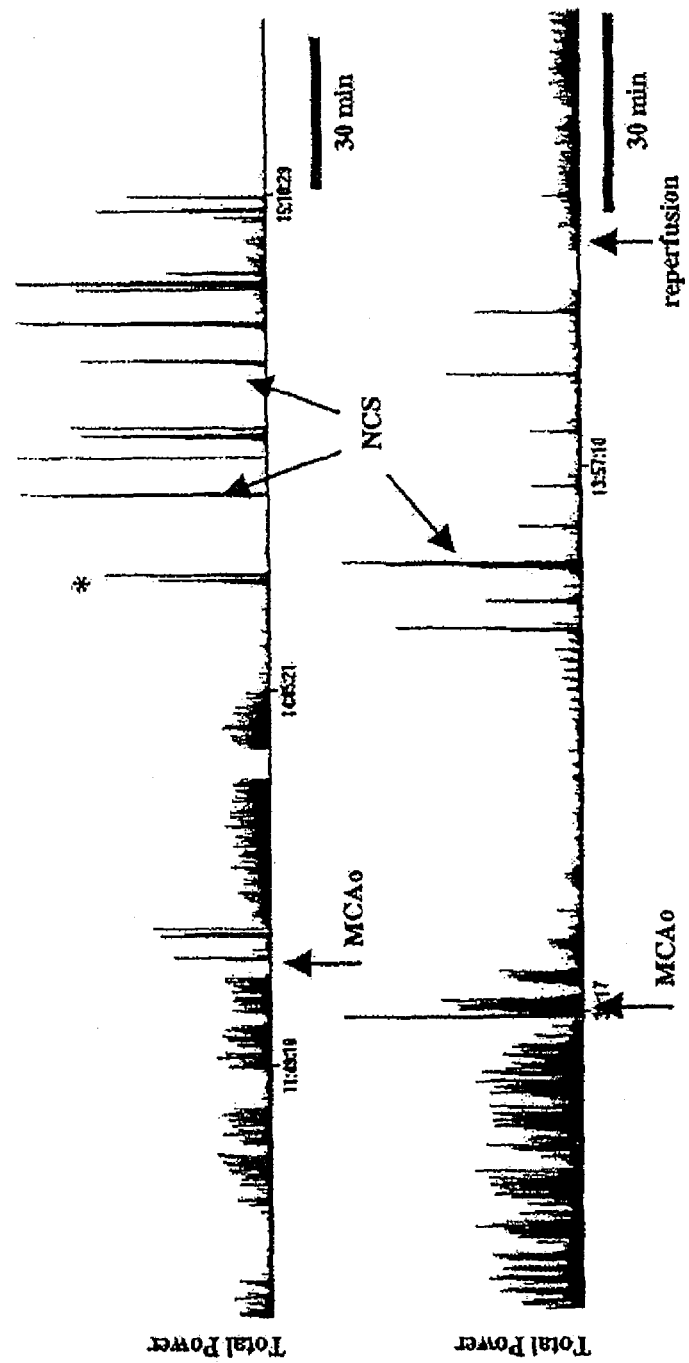
FIG. 22D depicts a continuous EEG trace showing total power of the EEG electrical activity of a rat with MCAo. The portion of the trace with an asterisk (*) is shown in expanded view in FIGS. 22A and 22B. Non-convulsive seizures (NCS) are shown (arrows).
FIG. 22E depicts a continuous EEG trace showing total power of the EEG electrical signal in another rat with MCAo. Non-convulsive seizures (NCS) are shown (arrows).
Figures 22F, 22G:
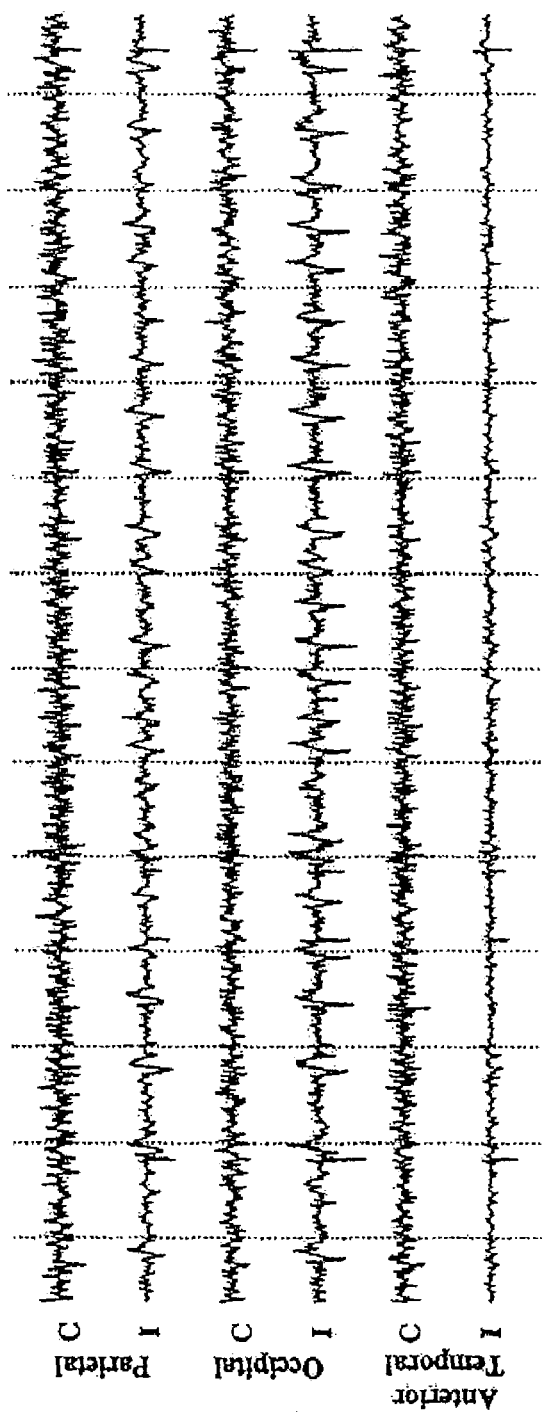
FIG. 22F shows EEG waveforms characteristic of periodic lateralized epileptiform discharges (PLEDs) recorded from contralateral (CC) and injured hemispheres (I) of a rat. Vertical lines represent 3-second intervals.
FIG. 22G shows an expanded view of a PLED obtained from an injured hemisphere. Vertical lines represent 3-second intervals.
Figure 22H:
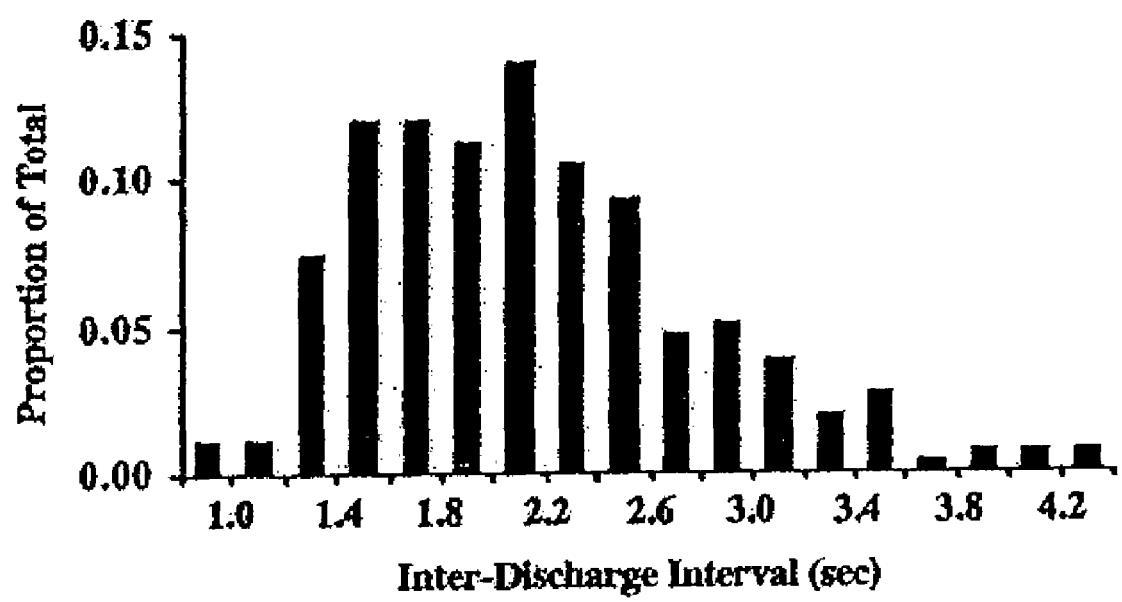
FIG. 22H shows the distribution of interdischarge intervals of PLEDs measured in a series of rats with unilateral MCAo.
Figure 22I:
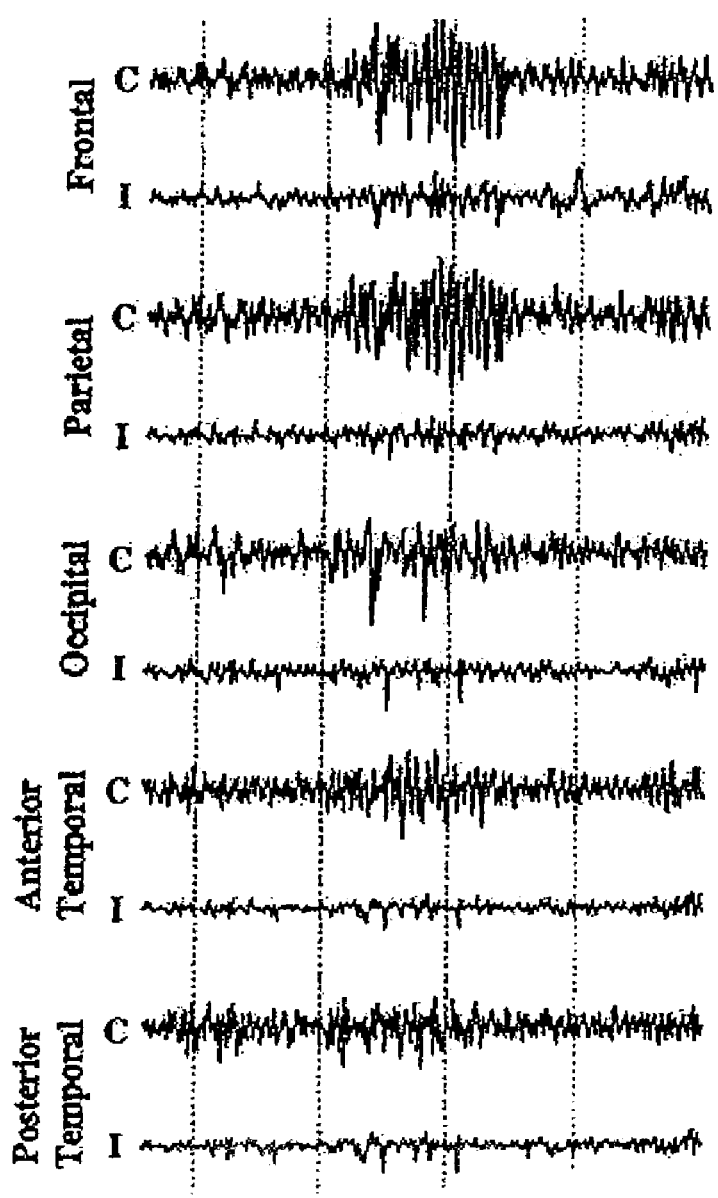
FIG. 22I shows the EEG waveform of intermittent rhythmic delta activity (IRDA) of contralateral (CC) and injured hemispheres recorded from different locations (frontal to posterior temporal) in the brain of a rat. Vertical lines represent 3-second intervals.
Figure 22J:
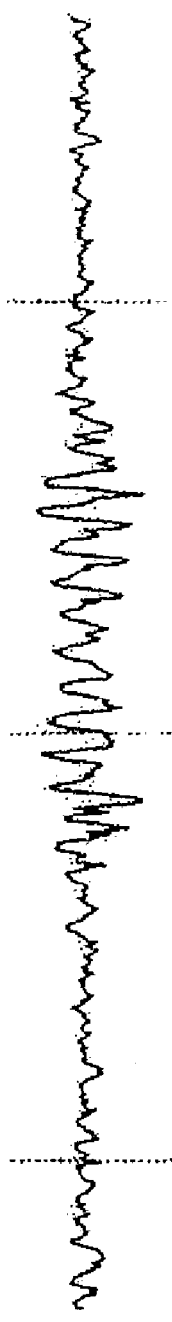
FIG. 22J shows an IRDA illustrated with an expanded time scale. Vertical lines represent 3-second intervals.
Figure 22K:
FIG. 22K shows a series of IRDAs. Vertical lines represent 3-second intervals.
Figure 22L:
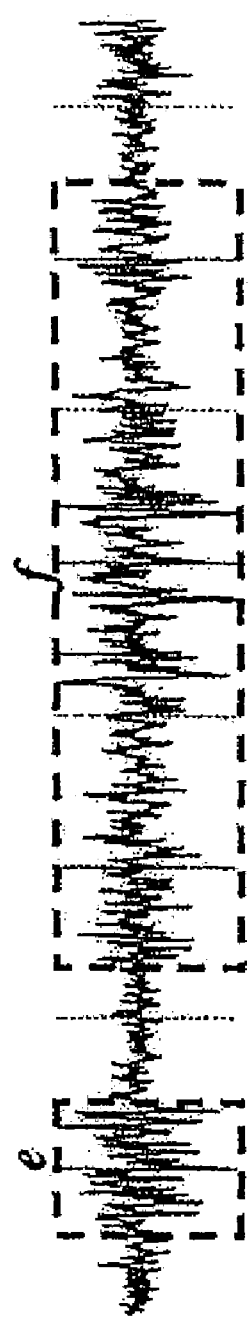
FIG. 22L shows examples of less rhythmic IRDAs in a rat with unilateral MCAo. The areas in dashed lines (e) and (f) are subjects of power spectra analysis shown in FIGS. 22M and 22N below. Vertical lines represent 3-second intervals.

Electroencephalographic traces were evaluated according to the methods of Hartings et al., Experimental Neurology 179:139-149 (2003), expressly incorporated herein fully by reference. Animals were evaluated for the presence of EEG patterns shown in FIGS. 22A to 22N. For animals exhibiting abnormal EEG patterns, the inter-discharge interval was determined and expressed as a proportion of the total as shown by FIG. 22H. For portions of an abnormal EEG trace, the total power was determined as a function of frequency of the EEG spiking pattern as shown in FIGS. 22M and 22N.

Infarct Analysis and Neurological Scoring

Triphenyltetrazolium chloride was used to visualize and quantitate the area of brain infarction from seven coronal brain slices, which were integrated to obtain a final core infarct volume (Inquiry Digital Analysis System; Loats Assoc., Westminster, Md.) (Tortella et al., 1999, Id.). Neurological scoring was based on a weighted 10-point scale, giving a positive score for each neurological deficit, including forelimb flexion, shoulder adduction, reduced resistance to lateral push, and contralateral circling (Tortella et al., Id.).

Statistical Analysis

Data are presented as the mean±standard error of the mean. Infarct analysis, neurological scoring, and off-line EEG analysis were performed by an experimenter blinded to the treatment group. Infarct volume and neurological scores were evaluated by Student t-test to compare individual treatments to the vehicle control group. Chi square test was used to assess treatment effects on NCS incidence, defined as the number of animals with and without identified NCS activity.

P values <0.05 were considered significant.

Results

Based on the time course of NCS occurrence described previously in the permanent MCAo model (Hartings et al., 2003), EEG activity was recorded continuously and NCS quantified over the 24-h period postinjury in both vehicle and G-2MePE-treated animals.

FIG. 22 shows an NCS discharge representative of those occurring in vehicle and drug treated animals. NCS events initiated as rhythmic spike or sharp wave discharges (FIG. 22B) with amplitudes increasing above baseline activity (FIG. 22A) and developed into sustained, large-amplitude rhythmic spike, spike/wave, sharp wave, or polyspike discharges (FIG. 22C). At termination, the seizure pattern generally became arrhythmic (FIG. 22D) with increased polyspike occurrence and decreasing discharge amplitude. No overt motor convulsions were visually observed during the electrographic seizures.

The number of NCS events per animal, total duration of NCS activity, average duration of individual NCS episodes, and latency to NCS onset post-occlusion for vehicle- and drug-treated groups were recorded.

Figure 23:
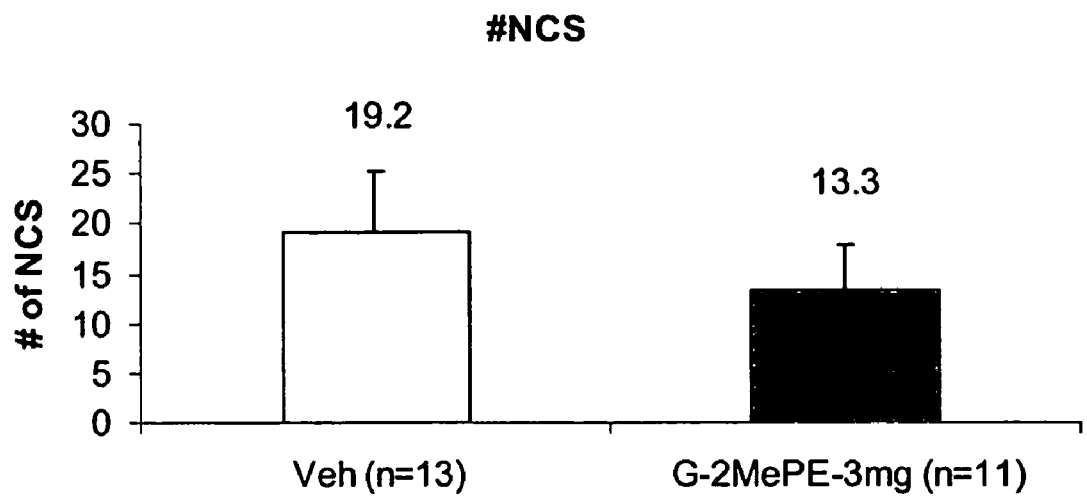
FIG. 23 shows the effect of G-2MePE administered as a 3.0 mg/kg bolus 30 min post MCAO immediately followed by 3 mg/kg/h infusion for 12 hours on post MCAo seizure activity on the number of non-convulsive seizures in vehicle-treated (n=13) and G-2MePE treated animals (n=11).
Figure 24:
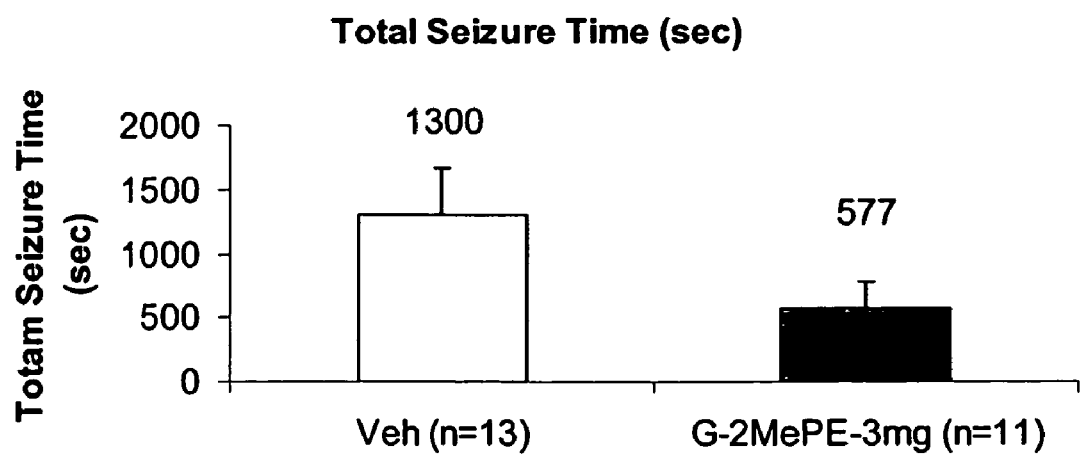
FIG. 24 shows the effect of G-2MePE administered as a 3.0 mg/kg bolus 30 min post MCAO immediately followed by 3 mg/kg/h infusion for 12 hours on total seizure time in vehicle-treated (n=13) and G-2MePE-treated animals (n=11).
Figure 25:
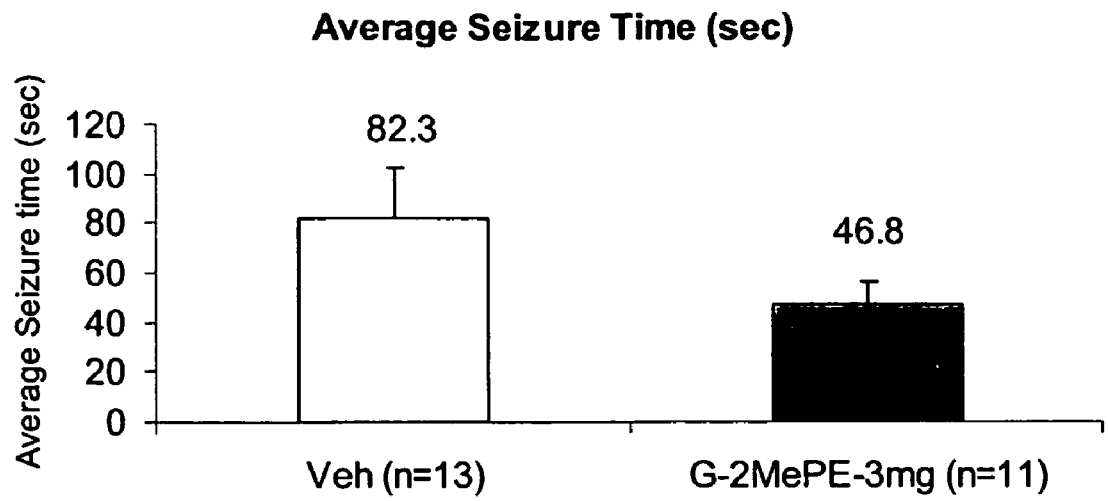
FIG. 25 shows the effect of G-2MePE administered as a 3.0 mg/kg bolus 30 min post MCAO immediately followed by 3 mg/kg/h infusion for 12 hours on average seizure time in vehicle-treated (n=13) and G-2MePE-treated animals (n=11).
Figure 26:
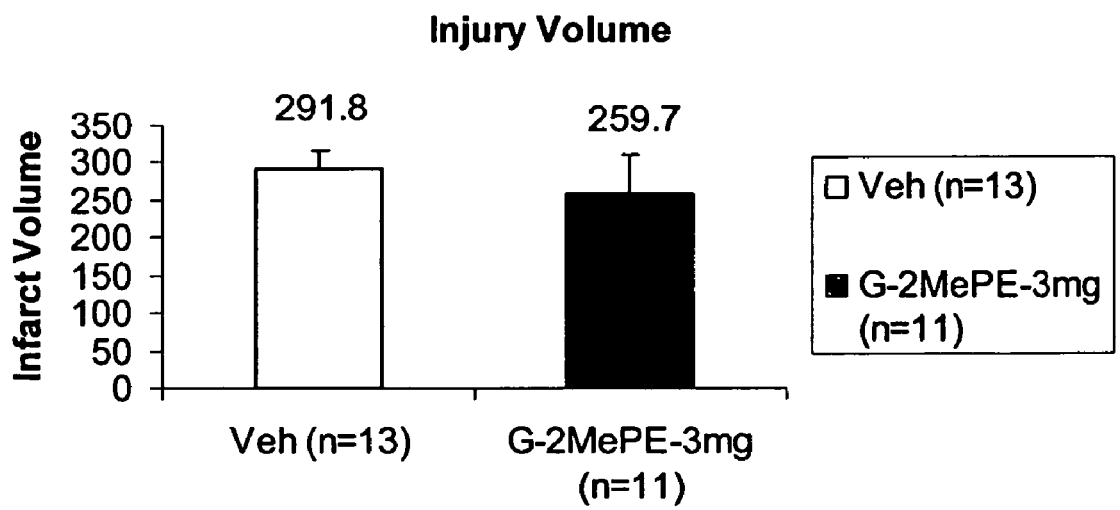
FIG. 26 shows the effect of G-2MePE administered as a 3.0 mg/kg bolus 30 min post MCAO immediately followed by 3 mg/kg/h infusion for 12 hours on total injury volume in vehicle-treated (n=13) and G-2MePE-treated animals (n=11).
Figure 27:
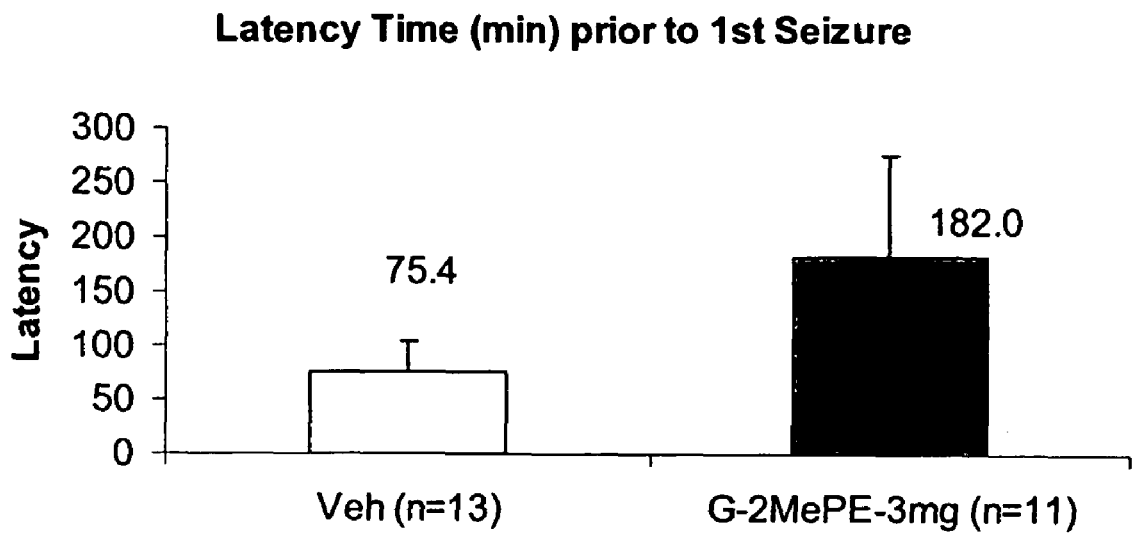
FIG. 27 shows the effect of G-2MePE administered as a 3.0 mg/kg bolus 30 min post MCAO immediately followed by 3 mg/kg/h infusion for 12 hours on post MCAO seizure activity on the latency to seizure in vehicle-treated (n=13) and G-2MePE-treated animals (n=11).
Figure 28:
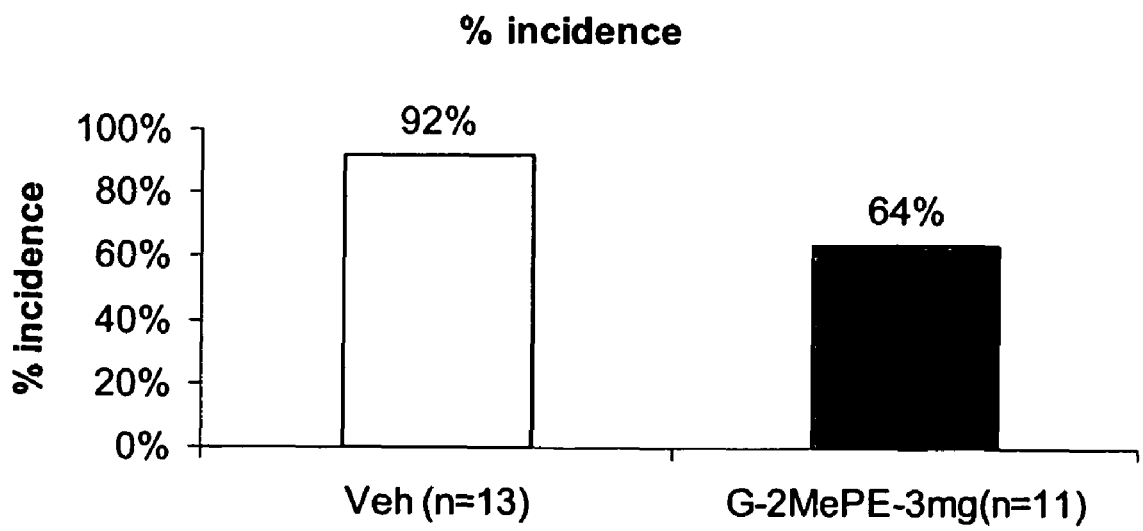
FIG. 28 shows the relative numbers of animals having seizures in vehicle-treated (n=13) and G-2-MePE-treated animals (n=11).

G-2MePe treated rats displayed 36% reduction in the number of NCS (FIG. 23), 60% reduction in the average time of NCS (FIG. 24), 56% reduction in the total time of NCS (FIG. 25) in comparison to the vehicle treated group. The infarct size was reduced on average by 19% in the drug-treated group (FIG. 26) and the Neurological Scoring at 24-h post-occlusion was improved by 18% in the treatment group (data not shown). The average latency to seizure was 125 min in vehicle group and 413.2 min in the treatment group (FIG. 27). (P<0.05)

The total incidence of seizure activity was 92% in vehicle-treated animals and 64% in animals treated with G-2MePE.

CONCLUSION

G-2MePE treatment attenuated the level of seizure activity measured by reduction of the number of non-convulsive seizures, average seizure time and total seizure time and increase in latency to seizure onset. G-2MePE also resulted in a decrease in infarct size. We conclude that G-2MePE can be an effective treatment for animals experiencing non-convulsive seizures.

The invention claimed is:

1. A method of treating an animal having a brain injury and an electroencephalographic (EEG) pattern characteristic of a non-convulsive seizure (NCS), comprising administration to an animal in need thereof a therapeutically effective amount of a neuroprotective agent which is glycyl-L-2-methylpropyl-L-glutamate (G-2MePE).

2. The method of claim 1, wherein said therapeutically effective amount is sufficient to reduce frequency of NCS.

3. The method of claim 1 where the injury is traumatic brain injury.

4. The method of claim 1 where said injury is caused by hypoxia/ischemia.

5. The method of claim 3 where said injury is penetrating brain injury.

6. The method of claim 4 where said injury is hypoxic brain injury.

7. The method of claim 4 where said injury is ischemic brain injury.

8. The method of claim 1 where said injury is perinatal asphyxia.

9. The method of claim 1, where said injury is a toxic injury.

10. The method of claim 1 where at least one other neuroprotective agent is administered.

11. The method of claim 1, where said injury is characterized by loss of neural cells from said animal's brain.

12. The method of claim 1, where said injury is caused by coronary artery bypass graft surgery.

13. The method of claim 1, where said injury is further characterized by a motor disorder.

14. The method of claim 13, where said motor disorder is a disorder of gait.

15. The method of claim 1, where said injury is of cortical cells, striatal cells, or cerebellar cells.

16. The method of claim 1, where said injury is characterized by an increase in astrocytic or microglial cell activation within the said animal's brain.

17. The method of claim 1, wherein said EEG pattern includes periodic lateralized epileptiform discharges.

18. The method of claim 1, wherein said effective amount is in the range of about 0.01 mg/kg/hr to about 10 mg/kg/hr.

19. The method of claim 1, further comprising administering one or more drugs selected from the group consisting of phenytoin, fos-phenytoin, mephenytoin, ethotoin, phenobarbital, mephobarbital, primidone, phenylethylmalonamide (PEMA), carbamazepine, ethosuximide, valproic acid, valproate, trimethadione, paramethadione, clonazepam, clorazepate, lorazepam, diazepam, N-desmethyldiazepam, oxazepam, gabapentin, lamotrigine, γ-vinyl, gamma amino butyric acid (γ-vinyl GABA), a carbonic anhydrase inhibitor, acetazolamide, flbamate, dazolam and dextromethorphan.

* * * * *